US010162481B2

(12) United States Patent
Robberechts et al.

(10) Patent No.: US 10,162,481 B2
(45) Date of Patent: Dec. 25, 2018

(54) METHOD AND SYSTEM FOR CREATING A FOOD OR DRINK RECIPE

(71) Applicant: FOODPAIRING NV, Brugge (BE)

(72) Inventors: Dries Robberechts, Wondelgem (BE);
Bernard Lahousse, Kortrijk (BE);
Peter Coucquyt, Deerlijk (BE); Johan Langenbick, Aalter (BE)

(73) Assignee: FOODPAIRING NV, Brugge (BE)

( * ) Notice: Subject to any disclaimer, the term of this patent is extended or adjusted under 35 U.S.C. 154(b) by 435 days.

(21) Appl. No.: 14/165,455

(22) Filed: Jan. 27, 2014

(65) Prior Publication Data

US 2015/0212661 A1    Jul. 30, 2015

(51) Int. Cl.

| G06F 3/0482 | (2013.01) |
|---|---|
| G06F 3/0484 | (2013.01) |
| G06Q 10/04 | (2012.01) |
| G06Q 10/06 | (2012.01) |
| G06Q 10/08 | (2012.01) |
| G06Q 50/12 | (2012.01) |
| G09B 19/00 | (2006.01) |
| G07F 9/02 | (2006.01) |
| G07F 13/06 | (2006.01) |

(52) U.S. Cl.
CPC ........ *G06F 3/0482* (2013.01); *G06F 3/04842* (2013.01); *G06Q 10/04* (2013.01); *G06Q 10/06* (2013.01); *G06Q 10/087* (2013.01); *G06Q 50/12* (2013.01); *G09B 19/0092* (2013.01); *G07F 9/023* (2013.01); *G07F 13/065* (2013.01)

(58) Field of Classification Search
CPC .............................. G06F 3/0482; G07F 13/065
See application file for complete search history.

(56) References Cited

U.S. PATENT DOCUMENTS

| 2005/0216285 | A1 | 9/2005 | Barroso |
|---|---|---|---|
| 2007/0073557 | A1 | 3/2007 | Abramson |
| 2008/0235100 | A1 | 9/2008 | Armstrong |
| 2008/0300993 | A1 | 12/2008 | Rozenblatt |
| 2009/0009815 | A1* | 1/2009 | Karasik ............. G06F 17/30634 358/403 |
| 2010/0217420 | A1 | 8/2010 | Sinclair |
| 2012/0136751 | A1 | 5/2012 | Ochtel |
| 2012/0303470 | A1 | 11/2012 | Arsenault |

(Continued)

FOREIGN PATENT DOCUMENTS

JP    2003-151028 A    5/2003

OTHER PUBLICATIONS

International Search Report and Written Opinion issued in connection with International Application No. PCT/IB2015/000678, 12 pages.

(Continued)

*Primary Examiner* — Omar R Abdul-Ali

(74) *Attorney, Agent, or Firm* — DLA Piper LLP (US)

(57) ABSTRACT

Disclosed herein are methods for creating a food or drink recipe and systems for implementing the same. Ingredients in the food or drink recipe are combined to create a desired characteristic of the end food or drink product. Some or all of the ingredients can be subject to one or more methods of preparation. The ingredients are selected based on compatibility between pairs of ingredients.

21 Claims, 6 Drawing Sheets

(56) References Cited

U.S. PATENT DOCUMENTS

| 2013/0149675 A1* | 6/2013 | Slone .................... G09B 19/00 |
| | | 434/127 |
| 2013/0149679 A1 | 6/2013 | Tokuda |
| 2013/0222406 A1 | 8/2013 | Wolfe |
| 2014/0188566 A1† | 7/2014 | Pinel |
| 2015/0058065 A1 | 2/2015 | Pinel |

OTHER PUBLICATIONS

Zoulias et al., Effect of fat and sugar replacement on cookie properties—Journal of the Science of Food and Agriculture, 1637-1644 (2002)—(8 pgs.).
European Application No. 15732037.5—Examination Report dated May 17, 2017 (6 pgs.).
PCT International Application No. PCT/IB2015/000678—International Preliminary Report on Patentability dated Aug. 2, 2016 (8 pgs.).
Belgium Patent Application No. 2016/5068—Office Action in Dutch dated Dec. 9, 2016 (12 pgs.).

\* cited by examiner
† cited by third party

METHOD AND SYSTEM FOR CREATING A FOOD OR DRINK RECIPE

FIELD

The present invention relates to a method for creating a new food or drink recipe and a computer implemented method for creating a new food or drink recipe. In addition the present invention relates to a system for creating a new food or drink recipe.

BACKGROUND

In general, creating new food or drink recipes involves several processes, namely trying to find new combinations of ingredients, then secondly, upon finding a new combination, trying to apply the new combination in a basic recipe, and thirdly making the basic recipe evolving to a well-balanced recipe and finding the optimum quantity of each ingredient.

Every experienced cook, kitchen chef, or cocktail maker is aware that each of these processes is an extensive, iterative, therefore extremely time-consuming job involving high costs and ingredient waste.

Moreover, another problem is that new combinations of ingredients do not always have the potential for evolving to a recipe for an end product with desired characteristics. In other words, a new combination of ingredients matching with regards to taste and flavor cannot automatically being used in a recipe for an end product with a particular characteristic. Consequently, in a lot cases the effort and cost involving finding new combinations does not result in a new food or drink recipe.

State of the art methods attempting to alleviate the process of finding the optimum quantity of each ingredient of a known recipe are known. For example, US Patent Publication No. 2013/0149679 describes a method for virtually optimizing a known recipe by calculating optimized amounts of ingredients based on target taste and aromatic values.

These methods only allow optimization of known recipes, i.e., recipes using known working combinations of ingredients and known quantities of ingredients more or less achieving an end product with desired characteristics.

Person skilled in the art will recognize that the state of the art methods however do not alleviate the process of investigating new combinations of ingredients, of investigating the potential of new combinations for resulting in a working recipe, of investigating the potential of a new combination for being used in a recipe for an end product with a particular characteristic, and of investigating the potential of a known combination of ingredients used in a particular type of end product for using in another type of end product.

In addition, state of the art methods are not prepared for or adapted to the following trends and developments in cooking and recipe development for a number of reasons.

Consumers want their personalized food or drink optimized for health, taste, cost, and mood. Consumers and even food professionals don't have the knowledge, nor time to customize a dish for each customer. Kitchen tools will take on this role, but they need to be powered by software that can fulfill the customers' needs instantly.

Food budget for 50% of U.S. families is less than 125 USD per week. A limited budget forces consumers towards more high energy dense and unhealthy food types. There is an urgent need to make cheap food also healthy. Government, insurance companies and food companies try to educate consumers through the use of applications to choose for healthy and tasteful food solutions with limited spending, but they are not able to generate a customized recipe for all.

A vast amount of people have a boring single dimensional food pattern leading to e.g., excess weight gain. 150 million citizens in the U.S. today are living with some form of a chronic disease or have special dietary restrictions. Since, each of those persons wants to have a personalized solution, there is a need for personalized dietary solutions. 80% of cases of cardiac disease, stroke, type 2 diabetes and 40% of cancers could be avoided through improved lifestyle choices, including those related to diet (WHO, 2011). For example, when a diabetes type 2 patient is diagnosed, a doctor provides caloric and macronutrient recommendations but such recommendations are abstract to the average individual. Therefore, an application is needed for teaching patients to gradually remove certain foods from their diets and replace them with better, healthier choices through the creation of new, personalized and creative recipes. These recipes will take patient metrics into consideration, thereby serving as a self-teaching tool for patients.

The digital kitchen is becoming a reality. The majority of consumers in the U.S. now use mobile food ordering tools. Mobile users are clearly looking for benefits to motivate them into transitioning their food ordering experience to smart phone applications (IAB, 2013).

Taking the above into consideration, it is a general object of the present invention to provide a method for creating a new food or drink recipe that decreases the iterative, time-consuming, and expensive character of creating new food or drink recipes.

Another general object of the present invention is to provide a method for creating a new food or drink recipe that decreases waste of ingredients, and/or decreases overstock, and/or optimizes the cost, profit or margin on a recipe, and/or optimizes the nutritional requirements of a recipe, and/or maximizes sustainability of a recipe, and/or maximizes/minimizes the quantity of certain ingredients in a recipe, and/or maximizes health benefits.

Further, a particular object of the present invention is to provide a method for creating a new food or drink recipe allowing cooks, consumers and cocktail makers and to find new combinations of ingredients with potential for being used in a recipe for an end product with desired characteristics, and to immediately develop the new combination up to the level of the final recipe.

In addition, it is also an object of the present invention to provide a computer implemented method and a system for creating a new food or drink recipe meeting the above objects.

SUMMARY OF THE INVENTION

Provided herein are the methods and systems for providing a food or a drink recipe. One of skill in the art would understand that any of the embodiments described herein can be used in combination with each other when possible, even with respect to different aspects of the invention.

In one aspect, provided herein is a method for providing a food or drink recipe on a computer device in response to a selection from a user. The method comprises the steps of receiving, from the user via an interface on a computer device, an end product (e.g., step 110); receiving, from the user and via the interface, a desired characteristic of the end product (e.g., step 120); receiving, from the user and via the interface, a first ingredient appropriate for being used in the end product, wherein the first ingredient is entered by the user or selected by the user from one or more first ingredients appropriate for creating the desired characteristic of the end product (e.g., step 130); and receiving, from the user and via the interface, at least one second ingredient, where the at least one second ingredient is entered by the user or selected by the user from one or more second ingredients, where the at least one second ingredient, when combined with the first ingredient, is suitable for creating an actual characteristic that approaches the desired characteristic (e.g., step 140). The method may additionally and optionally comprise the step of receiving, from the user and via the interface, a preparation method, which may assist in reach the desired characteristic; receiving, from the user and via the interface, a composition frame, which may be used as a guide for ingredient selection.

In some embodiments, the method further comprises a step of providing, to the user via the interface, the one or more end products. In some embodiments, the method further comprises a step of providing, to the user via the interface, the one or more desired characteristics. In some embodiments, the method further comprises a step of providing, to the user via the interface, the one or more first ingredients. In some embodiments, the method further comprises a step of providing, to the user via the interface, the one or more second ingredients.

In some embodiments, a preparation method is applied to the first ingredient or the at least second ingredient before they are combined to create an actual characteristic that approaches the desired characteristic. In some embodiments, the preparation method is selected from the group consisting of a cooking technique, a cocktail preparation technique, a baking technique, a processing technique, and a combination thereof.

In some embodiments, the method further comprises a step of providing, to the user via the interface, a preparation method based on the first ingredient or the at least second ingredient, whereby the first ingredient or the at least second ingredient is prepared according to the preparation method before they are combined to create an actual characteristic that approaches the desired characteristic.

In some embodiments, the method further comprises a step of rendering a food or drink recipe comprising the first ingredient at a first quantity and the at least one second ingredient at a second quantity, wherein the first and second quantities are suitable for creating an actual characteristic that approaches the desired characteristic (e.g., step 160).

In some embodiments, the first quantity or second quantity is varied to create variations of the food or drink recipe. In some embodiments, the quantity of one of the ingredients is determined additionally based on a desired intensity value of the ingredient in the end product. In some embodiments, the quantity of each ingredient is determined such that an absolute intensity of each of the ingredients is identical.

In some embodiments, the method further comprises a step of receiving, from the user and via the interface, at least one third ingredient, wherein the at least one third ingredient is entered by the user or selected by the user from one or more third ingredients and is suitable, when combined with the first ingredient and the at least second ingredient, for creating an actual characteristic that approaches the desired characteristic (e.g., step 150).

In some embodiments, the method further comprises a step of providing, to the user via the interface, the one or more third ingredients.

In some embodiments, the method further comprises a step of providing, to the user via the interface, a third quantity of the at least one third ingredient.

In some embodiments, the method further comprises a step of rendering a food or drink recipe comprising the first ingredient at a first quantity, the at least one second ingredient at a second quantity, and the at least one third ingredient at a third quantity, wherein the first, second and third quantities are suitable for creating an actual characteristic that approaches the desired characteristic.

In some embodiments, any one of the first, second or third quantities is varied to create variations of the food or drink recipe.

In some embodiments, the computer device is selected from the group consisting of a networked device, a local device, a vending machine, a food dispensing machine, a drink dispensing machine, an automated drink maker, an automated cocktail maker, an automated food preparation machine, a desktop computer, a laptop computer, a mobile device, a handheld device, a tablet, an iPad, a Kindle, a cellular phone, a smart phone, a personal digital assistant (PDA), a networked television, a networked media player, and a networked digital video recorder (DVR). In some embodiments, the computer device is connected to a printing or display device, via wireless or wired connection.

In some embodiments, the one or more end products are selected from the group consisting of a pastry, a meat dish, a seafood dish, a fish dish, a salad, a mixed drink, a confectionary type, a dissert, a vegetable dish, and a soup.

In some embodiments, the one or more desired characteristics are created based on the end product selected by the user. In some embodiments, the desired characteristic represents a taste, a flavor, a smell, a texture, or a color, or a combination thereof.

In some embodiments, the one or more first ingredients are created based on the desired characteristic selected by the user.

In some embodiments, the one or more second ingredients are compatible with the first ingredient selected by the user. In some embodiments, each of the one or more second ingredients has a compatibility score with the first ingredient that is above a set value. In some embodiments, the one or more second ingredients are created based on the end product selected by the user. In some embodiments, the at least one second ingredient is selected based on the first ingredient selected by the user. In some embodiments, the one or more third ingredients are created based on the end product selected by the user. In some embodiments, the at least one third ingredient is selected based on the first or at least one second ingredient selected by the user. In some embodiments, the at least one third ingredient is selected based on the first and at least one second ingredient selected by the user.

In some embodiments, the interface is provided by a computer program product. In some embodiments, the interface is provided by web-based interface, an executable computer program, or a mobile application.

In one aspect, provided herein are a method for providing a food or drink recipe. The method comprises the steps of receiving, from a user via an interface on a computer device, one or more ingredients, wherein the one or more ingredients are entered by the user or selected by the user using the interface from a plurality of ingredients (e.g., step 210); receiving, from the user and via the interface, an end characteristic, wherein the end characteristic is associated with at least one of the one or more ingredients, and wherein the end characteristic is selected from the group consisting of an end product, a desired characteristic and a combination thereof, each of which being associated with the at least one of the one or more ingredients (e.g., step 220); and providing, to the user via the interface, a food or drink recipe comprising a quantity for each of the one or more ingredients, thereby creating an actual characteristic that approaches the end characteristic (e.g., step 230). Additionally and optionally, the method provided herein includes a step of providing a method of preparation for one or more ingredients. Further, the method optionally includes a step where the user makes selection via the interface, a composition frame. The composition frame can be used as a guide for ingredient selection. One of skill in the art would understand that the method of preparation can vary depending on the ingredients and their quantities.

In one aspect, provided herein are a computer program product for use in conjunction with a computer having a processor and a memory connected to the processor, the computer program product comprising a computer readable storage medium having a computer program mechanism encoded thereon, wherein the computer program mechanism may be loaded into the memory of the computer and cause the computer to carry out the method of any one of the embodiments or any combinations thereof.

In one aspect, provided herein are a method for creating a food or drink recipe. The method comprises the steps of selecting, via an interface on a computer device, a type of end product, wherein the end product is selected by the user from one or more end products (e.g., step 310); selecting, via the interface, a desired characteristic of the end product, wherein the desired characteristic is selected by the user from one or more desired characteristics (e.g., step 320); selecting, via the interface, a first ingredient appropriate for being used in the end product, wherein the first ingredient is selected by the user from one or more first ingredients appropriate for being used in the end product (e.g., step 330); and selecting, via the interface, at least one second ingredient, wherein the at least one second ingredient is selected by the user from one or more second ingredients, wherein the at least one second ingredient, when combined with the first ingredient, is suitable for creating an actual characteristic that approaches the desired characteristic (e.g., steps 340 and 350). Additionally and optionally, the method comprises the step of selecting, via an interface on a computer device, a method of preparation for each ingredient or a combination thereof and/or the step of selecting a step of selecting a composition frame.

In some embodiments, the method further comprises a step of causing, via the interface, a food or drink recipe to be rendered, wherein the food or drink recipe comprises the first ingredient at a first quantity and the at least one second ingredient at a second quantity (e.g., step 136).

In some embodiments, the method further comprises a step of receiving, via the interface, a preparation method based on the first ingredient or the at least second ingredient, whereby the first ingredient or the at least second ingredient is prepared according to the preparation method before they are combined to create an actual characteristic that approaches the desired characteristic.

In some embodiments, the method further comprises a step of selecting, via the interface, a composition frame, wherein the composition frame comprises one or more ingredient types for further selection.

In one aspect, provided herein is a system for creating a food or drink recipe. The system comprises a database comprising different types of end products and a means for allowing selection of a type of end product, a means for allowing selecting a desired characteristic of the end product, a means for providing a selection of one or more first ingredients appropriate for being used in the selected type of end product, and for allowing selecting one or more of the first ingredients, a means for providing a selection of one or more second ingredients by their compatibilities with the first ingredient, the one or more second ingredients suitable for approaching the characteristic, and for allowing selecting one or more of the second ingredients, and a means for calculating quantities of the selected first and second ingredients, the quantities being appropriate for approaching the characteristic. Additionally, the system comprises a database comprising different methods of preparation and a means for allowing selection of a method of preparation, a means for allowing selecting a composition frame.

In some embodiments, the method further comprises a step of a means for allowing a selection of preparation method for at least one of the one or more first ingredients or the one or more second ingredients.

In some embodiments, the means for providing a selection of the one or more second products is adapted for restricting the selection based on the type of end product. In some embodiments, the means for providing a selection of the one or more second products is adapted for linking the type of end product to a composition frame consisting of a number of ingredient types and for repeating providing a selection and allowing selecting of one or more second ingredients until at least one ingredient is selected for each ingredient type by its compatibility with the first ingredient and/or one or more or all of the already selected second ingredients.

In some embodiments, the means for allowing selecting a desired characteristic is adapted for selecting a taste, a flavor, a smell, a texture, or a color, or a combination thereof. In some embodiments, the means for allowing selecting a desired characteristic is adapted for selecting a matrix of at least two numerical values.

In some embodiments, the means for calculating appropriate quantities is adapted for additionally calculating the appropriate quantities based on the desired intensity value of an ingredient in the end product. In some embodiments, the means for calculating appropriate quantities are adapted for calculating the appropriate quantities additionally based on physical and/or technical requirements corresponding to a cooking formulation.

Also provided is a computer program product for use in conjunction with a computer having a processor and a memory connected to the processor, the computer program product comprising a computer readable storage medium having a computer program mechanism encoded thereon, wherein the computer program mechanism may be loaded into the memory of the computer and cause the computer to carry out the method of any of the embodiments or combination of embodiments described herein.

BRIEF DESCRIPTION OF THE DRAWINGS

Those of skill in the art will understand that the drawings, described below, are for illustrative purposes only. The drawings are not intended to limit the scope of the present teachings in any way.

DESCRIPTION OF THE INVENTION

Figure 1:
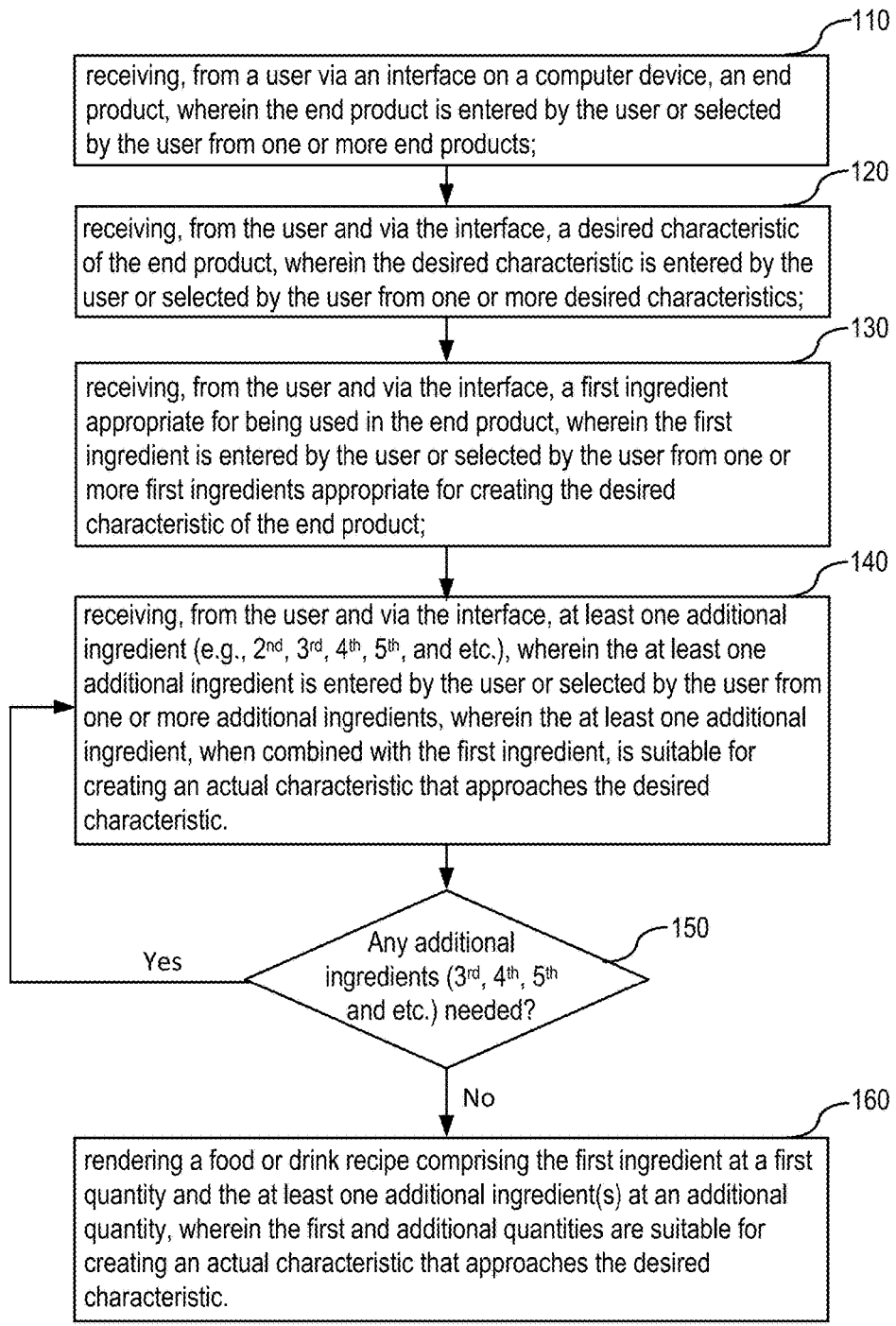
FIG. 1 illustrates an exemplary embodiment in accordance with the invention.

Disclosed herein are the methods and systems for providing a food or a drink recipe and applications thereof. One of skill in the art would understand that any of the embodiments described herein can be used in combination with each other when possible.

Compatibility Score or Rank

As used herein, the term "compatibility score or rank" should be broadly construed as referring to the extent to which a food or drink ingredient matches with another food or drink ingredient in any combination. In some cases, two ingredients have a high compatibility score or rank if they share one or more key components (e.g., a key flavor component and/or a key aromatic component) within a defined concentration. In some cases, two ingredients have a high compatibility score or rank if the key components generate a synergistic effect. For example, a score or rank can be assigned based on a scoring or ranking matrix that is pre-determined based on quantitative or non-quantitative empirical data. Compatibility scoring or ranking is different from wine and food matching. Here, the terms "compatibility score" and "compatibility rank" are used interchangeably. It will be understood that a compatibility score or rank can vary between same ingredients, depending on the cooking and/or processing of one or both of the ingredients.

As provided herein, compatibility scoring or ranking is a method for identifying which ingredients match well together. For example, in a typical compatibility analysis, components of a target ingredient are compared with components of one or more candidate ingredients. The analysis will be done based on the principle that ingredients combine well with one another when they share key flavor and/or key aromatic components within a defined concentration depending on the application and matrix or if they generate a synergistic effect. In some embodiments, compatibilities are determined via pairwise analysis. In some embodiments, compatibilities are determined via group analysis.

The flavor or aroma compounds may be determined with the aid of gas chromatography, which in most cases is coupled with a mass spectrometer (GC-MS) or other devices. Key aromas may be identified by comparing the concentrations of the aromas with their respective flavor threshold in the same matrix or other analytical methods, and may be defined as every compound that is present in concentrations higher than their specific flavor threshold and that a human will effectively smell. Flavor components below the flavor threshold can become key flavors through interactions with other flavor components. Interactions between flavor components are checked through the effect of flavor dilutions.

Once the most important flavor components of the ingredient have been analyzed, they are compared to a database of hundreds of other ingredients, and ingredients with key flavor within a defined concentration and aroma components interactions with the original ingredient are retained.

In some embodiments, the results from compatibility scoring or ranking analysis of a target ingredient are rendered as a list with the most compatibility ingredients listed at the top. In some embodiments, the results are graphically presented in a two dimensional representation such as a compatibility scoring or ranking tree. The compatibility scoring or ranking tree is used as a visual aid for cooks and cocktail makers to indicate which ingredients might match from a flavor and aromatic perspective. For example, the target ingredient can be placed in the center of a map, and ingredients that are the most compatible with the target ingredient will be closely positioned to the target ingredient. The extent of the compatibility can be weighted and visually presented as a large font or a bigger graphic representation.

End Product

As used herein, the term "end product" should be broadly construed as referring to a type of food or drink category representing a collection of food products with common main characteristics. The categories can be based on food types (e.g., pastries, appetizers, soup, sandwich, pasta, pizza, lunch, dinner, snack, drinks, dessert, and etc.); cooking/processing techniques (baking, frying, steaming, roasting, hot processing, cold processing, marinating, salting, curing, pureeing, chopping, kneading, blending, grinding, poaching, and etc.), main ingredients (e.g., seafood, fish, meat, poultry; or vegetarian) or food taste (spicy, sweet, sour, bitter and etc.). The categories can also be based on cooking techniques (e.g., baking, frying, roasting, stir-frying, steaming, curing and etc.) and cuisine types (French, Italian, Chinese, Japanese, Indian, Fusion and etc.).

In some embodiments, it is possible to have multiple levels of end products. For example, a meat dish can be sub-divided into dishes with beef, lamb, pork and etc. as the main ingredient.

A person skilled in the art will appreciate that in the context of the present invention a type of end product does not mean a particular dish or mixed drink containing a particularly chosen ingredient. A type of end product should be understood as any type of food product representing a collection of food products with common main characteristics, such as for example:

Pastry types: shortcrust pastry, flaky pastry, puff pastry, choux pastry, quiches, cookies, breads etc.

Meat dish types: grills, meatloaf, sausages, salamis, meat pie, meat stew, pâté, etc.

Fish dish types: grills, fish stew, terrines, seafood and etc.

salad types and vegetarian dishes: vegetable salad, bound salad, fruit salad, etc.

mixed drink types: cocktails, sours, punches, mocktails, etc.

Confectionary types such as candies, toffees, pralines, ice-cream, etc.

Snacks such as chips, pop-corn, etc.

soups, broths, bouillons, fondue, sauces, mayonnaises, dressings, jellies, marmalades, chutneys, mousses, etc.

craft beers, wines, spirits

A person skilled in the art will further appreciate that the end product itself and its final recipe are unknown at the start of the recipe development process and that the cook, consumer, recipe developer, cocktail maker starts the process just by selecting a type of end product he desires to achieve.

Characteristics, Desired Characteristics and Actual Characteristics

As used herein, the term "characteristic" of an end product should be broadly construed as referring to any type of characteristic a food product, including but not limited to, e.g., a taste, a flavor, a smell, a texture, a color or combinations thereof. One or more such characteristics can be expressed as a value representing an extent of presence of one or more characteristics in the end product, thereby rendering a desired characteristic. The term "desired characteristic" can be used interchangeably with "target characteristic." Examples of such desired characteristics can be a defined sweetness, fattiness, and the like. In particular in a corresponding computer implemented method, such value representing an extent of presence of the characteristic can be a numerical value within a numerical range from no presence up to overpowering presence. The term "actual characteristic" of an end product should be broadly construed as referring to a characteristic that will likely be present in an end product based on the selected ingredients, each at a specified quantity.

In some embodiments, each ingredient and preparation method has an assigned characteristic, which serves as the foundation for calculating the actual characteristic and quantities to approach the desired characteristic. In some embodiments, an actual characteristic is a characteristic value that is expected to be presented in an end product corresponding to a food or drink recipe rendered based on methods and systems described herein. In some embodiments, an actual characteristic in an end product can be computed based on the quantities and characteristics of the ingredients, in addition to the characteristic of a method of preparation. The term "actual characteristic" can be used interchangeably with "expected characteristic," "calculated characteristic" or "obtained characteristic."

In some embodiments, a desired characteristic can be a value of sweetness, sourness, saltiness, bitterness, umami, pungency, coolness, numbness, astringency, metallicness, fattiness, heartiness and the like, or a combination thereof.

In some embodiments, a desired characteristic can also be a value of dryness, crumbliness, crispiness, crunchiness, brittleness, graininess, gumminess, hardness, moisture release, mouthcoating, slipperiness, smoothness, homogeneity, viscosity, or a combination thereof.

In some embodiments, the desired characteristic can be also a combination of different taste characteristics, different flavor characteristics, different smell characteristics, different texture characteristics, or different color characteristics, of it may be a combination of different types of characteristics.

In some embodiments, desired characteristics were determined by a taste panel including chefs, bartenders and consumers. In some embodiments, desired characteristics depend on type of dish (e.g., main dish versus dessert), countries/regions (cultural preferences), interaction of components in end product (interaction with e.g., proteins), temperature (cold versus hot).

In some embodiments, a user can start with known ingredients, therefore can obtained an end characteristic of the ingredients.

Composition Frame

As used herein, the term "composition frame" refers to a set of ingredient types. In some embodiments, for example, a composition frame comprises all the ingredient types eliciting characteristics that are required to converge to render the characteristic of an end product. In some embodiments, the composition frame is accessible after a user makes a selection at an interface. In some embodiments, the composition frame is provided as the interface for a user to make a selection. It will be understood that several different composition frames can converge to the characteristic of the same end product.

By selecting at least one ingredient for each ingredient type in an appropriate composition frame, it is mathematically guaranteed that the characteristic of the end product can be sufficiently reached by calculating the quantities of the selected ingredients. The ingredient types are typically defined in terms of a main characteristic and are populated with ingredients eliciting the same or similar characteristic e.g., acids, or sweet products. Alternatively ingredient types can correspond to the commonly known classes of ingredients, such as for example fats including oils, dairy products, herbs, spices, cereals, meat, fish, seafood, juices, alcohols, condiments, sweeteners, vegetables etc. The user then selects the first ingredient by choosing an ingredient belonging to an ingredient type used in the composition frame of the end product type. In a corresponding computer implemented method, a list of first ingredients may be automatically provided belonging to one of the ingredient types used in the composition frame and the user makes his choice from the list.

Likewise, also the second ingredient may be selected additionally based on the required ingredient types used in the composition frame of the end product type. It can belong to the same ingredient type as the first ingredient, but preferably to another ingredient type used in the composition frame of the end product type.

Preferably, the step of selecting a second ingredient is repeated until an ingredient is selected for each ingredient type required in the composition frame of the end product type.

It should be clear that a method in accordance with the present invention may be applied also without making use of composition frames. Indeed, selecting second ingredients can be done also via their compatibility scores or ranks combined with iterative calculation of what ingredients are most suitable for approaching the characteristic. In addition, iterative calculation may also provide whether the already selected second ingredients and their characteristics suffice for adequately converging to the desired characteristic of the end product.

Person skilled in art will recognize that by selecting second ingredients that match with the already selected ingredients from their compatibility scores or ranks perspective, that are appropriate for approaching a desired characteristic in the end product, and that represent each ingredient type in the composition frame of the end product type, development of a new recipe may be performed even faster and even more efficiently. "On-the-spot" recipe creation becomes possible.

Methods of Preparation

As used herein, the term "method of preparation" or "preparation method" refers to a process or technique by which an ingredient or a combination of ingredients is prepared. Preparation methods should be broadly construed to include any applicable methods and/or process of cooking, processing, assembling, making, and etc. Exemplary preparation methods include but are not limited to being shaken, being stirred, gassing, de-gassing, baking, frying, steaming, roasting, hot processing, cold processing, marinating, salting, curing, pureeing, chopping, kneading, blending, grinding, poaching, mixing, blending, and etc.

Exemplary Processes

Figure 2:
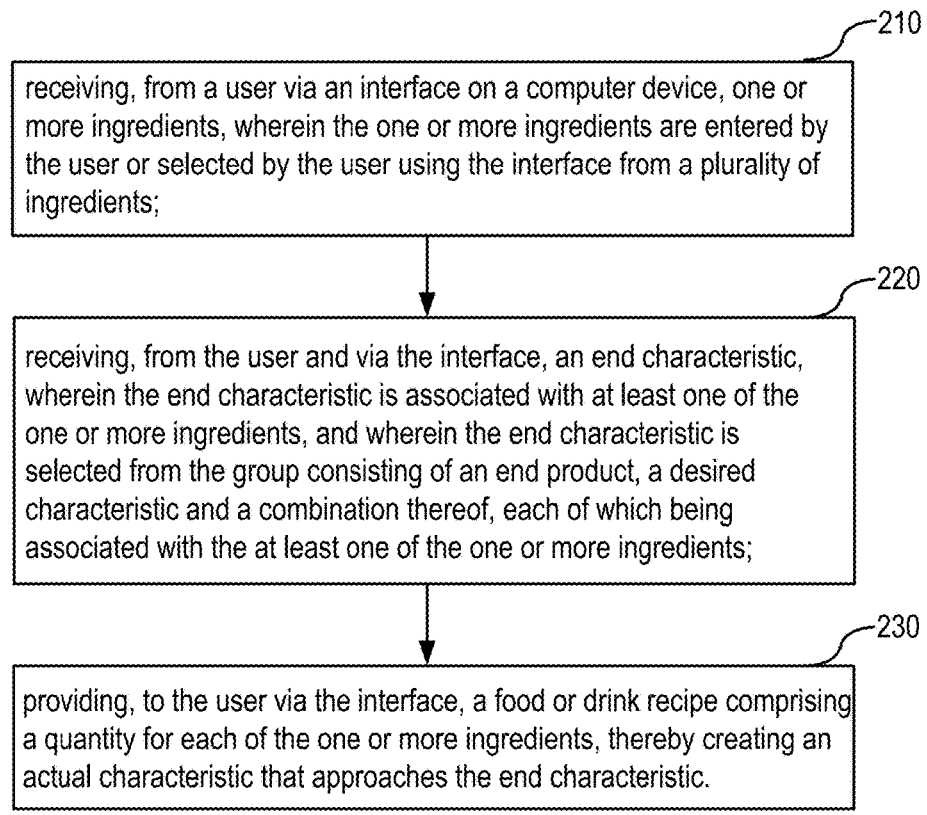
FIG. 2 illustrates an exemplary embodiment in accordance with the invention.
Figure 3:
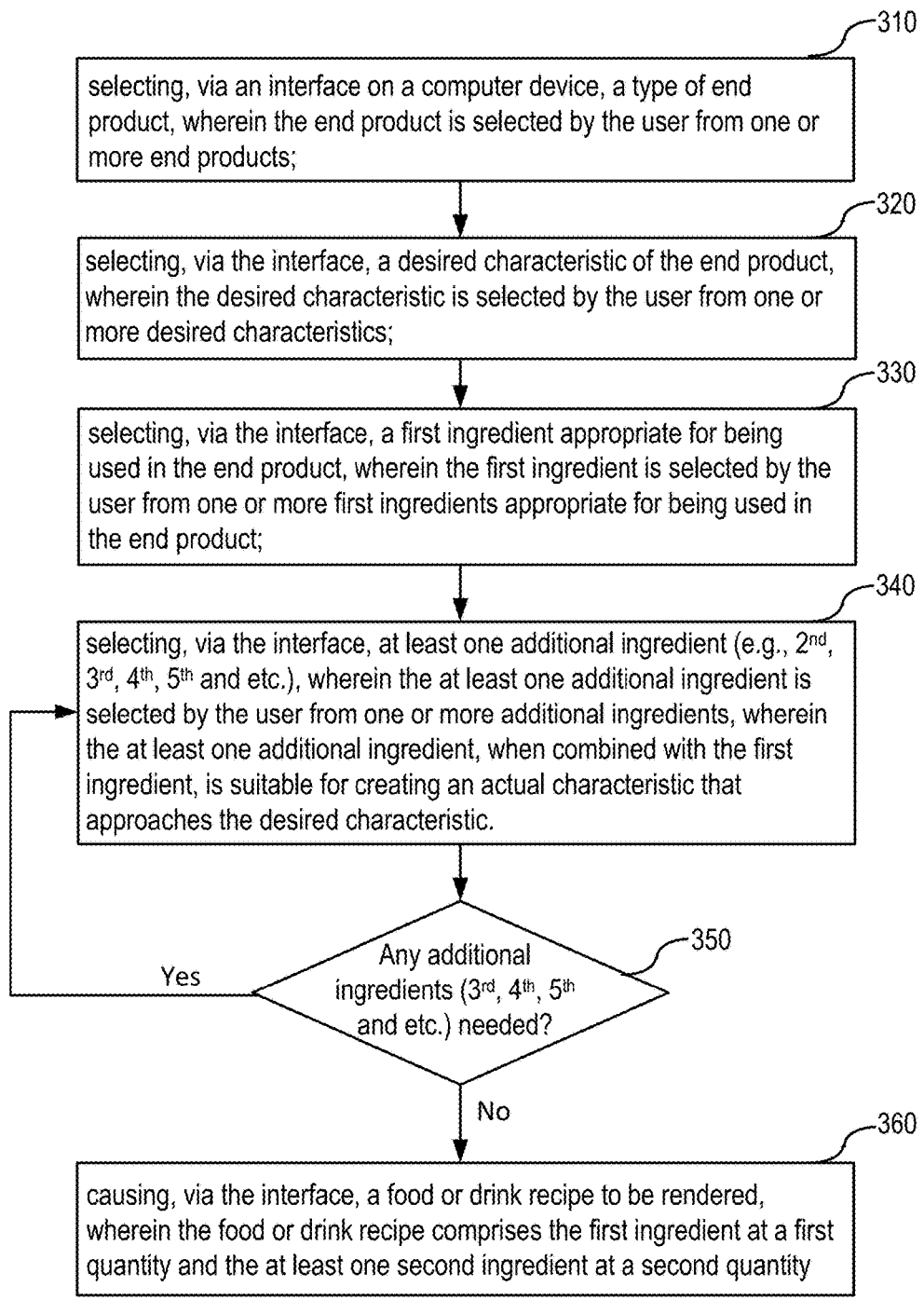
FIG. 3 illustrates an exemplary embodiment in accordance with the invention.

Provided herein are exemplary methods for providing a food or a drink recipe (e.g., FIGS. 1-3). One of skill in the art would understand that any of the embodiments described herein or variations thereof can be used in combination with each other when possible.

In one aspect, provided herein are a method for providing a food or drink recipe on a computer device in response to a selection from a user. The method comprises the steps of receiving, from the user via an interface on a computer device, an end product; receiving, from the user and via the interface, a desired characteristic of the end product; receiving, from the user and via the interface, a first ingredient appropriate for being used in the end product, wherein the first ingredient is entered by the user or selected by the user from one or more first ingredients appropriate for creating the desired characteristic of the end product; and receiving, from the user and via the interface, at least one second ingredient, where the at least one second ingredient is entered by the user or selected by the user from one or more second ingredients, where the at least one second ingredient, when combined with the first ingredient, is suitable for creating an actual characteristic that approaches the desired characteristic. The method additionally and optionally comprises the step of receiving, from the user and via the interface, a preparation method, which may assist in reach the desired characteristic; receiving, from the user and via the interface, a composition frame, which can be used as a guide for ingredient selection.

In some embodiments, the end product is entered by the user. In some embodiments, the end product is selected by the user from one or more end products. In some embodiments, a combination of manual entry and selection is done to render an end product. For example, as the user types, a list of possible choices of end products appear and then the user can select from the list. In some embodiments, the end product is a predefined constant and not selectable by user. In some embodiments, one or more ingredients in an end product can be a predefined constant and not selectable by user.

In some embodiments, the desired characteristic is entered by the user. In some embodiments, the desired characteristic is selected by the user from one or more desired characteristics. In some embodiments, the desired characteristic may be a predefined constant and not selectable by user. In some embodiments, a combination of manual entry and selection is done to render a desired characteristic. For example, as the user types, a list of possible choices of desired characteristics appear and then the user can select from the list.

In some embodiments, the preparation method is entered by the user. In some embodiments, the preparation method is selected by the user from one or more preparation methods. In some embodiments, the preparation method may be a predefined constant and not selectable by user. In some embodiments, a combination of manual entry and selection is done to render a preparation method. For example, as the user types, a list of possible choices of preparation methods appear and then the user can select from the list.

In some embodiments, the composition frame is entered by the user. In some embodiments, the composition frame is selected by the user from one or more composition frames. In some embodiments, the composition frame may be a predefined constant and not selectable by user. In some embodiments, a combination of manual entry and selection is done to render a composition frame. For example, as the user types, a list of possible choices of composition frames appear and then the user can select from the list.

In some embodiments, the method also comprises a step of providing, to the user via the interface, the one or more end products. In some embodiments, the method also comprises a step of providing, to the user via the interface, the one or more desired characteristics. In some embodiments, the method also comprises a step of providing, to the user via the interface, the one or more first ingredients. In some embodiments, the method also comprises a step of providing, to the user via the interface, the one or more second ingredients. In some embodiments, the method also comprises a step of providing, to the user via the interface, the one or more preparation methods. In some embodiments, the method also comprises a step of providing, to the user via the interface, the one or more composition frames.

In some embodiments, the suitability and/or compatibility between the at least one second ingredient and the first ingredient is determined by a predetermined compatibility score system. In some embodiments, the compatibility score system utilizes one or more scoring matrices.

In some embodiments, the method additionally and optionally includes a step of providing a method of preparation for one or more ingredients. In some embodiments, the method further optionally includes a composition frame (e.g., fruit-based, nut based ganache), through which a user can select and/or navigate among ingredient types. One of skill in the art would understand that the method of preparation varies depending on the ingredients and their quantities. For example, in some embodiments, a cooking technique is applied to the first ingredient and/or the at least second ingredient before they are combined to create an actual characteristic that approaches the desired characteristic. In some embodiments, the cooking technique is applied to increase the intensity of a desired characteristic in the end product. One of skill in the art would understand that such methods of preparation or selection/navigation via a composition frame, alone or in combination, can be applied to any embodiment described herein or variations thereof.

In some embodiments, the method also comprises a step of rendering a food or drink recipe comprising the first ingredient at a first quantity and the at least one second ingredient at a second quantity, where the first and second quantities are suitable for creating an actual characteristic that approaches the desired characteristic. In some embodiments, a method of preparation is used to create an actual characteristic that approaches the desired characteristic.

In some embodiments, a desired characteristic is subject to variations. For example, a user can select from a gradient scale to specify an element of the desired characteristic (e.g., mild, spicy, to extra spicy for a dish; or light, strong or extra strong for alcohol content in a cocktail) Accordingly, in such embodiments, the first quantity or second quantity is varied to create variations of the food or drink recipe.

In some embodiments, the method also comprises a step of receiving, from the user and via the interface, at least one third ingredient, wherein the at least one third ingredient is entered by the user or selected by the user from one or more third ingredients and is suitable, when combined with the first ingredient and the at least second ingredient, for creating an actual characteristic that approaches the desired characteristic. One of skill in the art would understand that additional ingredients can be included based on compatibilities.

In some embodiments, the method also comprises a step of providing, to the user via the interface, the one or more third ingredients. In some embodiments, the method also comprises a step of providing, to the user via the interface, a third quantity of the at least one third ingredient. In some embodiments, the method also comprises a step of rendering a food or drink recipe comprising the first ingredient at a first quantity, the at least one second ingredient at a second quantity, and the at least one third ingredient at a third quantity, wherein the first, second and third quantities are suitable for creating an actual characteristic that approaches the desired characteristic. One of skill in the art would understand that any or all of the ingredients can be subject to one or more methods of preparation.

In some embodiments, any one of the first, second or third quantities is varied to create variations of the food or drink recipe.

In some embodiments, the computer device is selected from the group consisting of a networked device, a local device, a desktop computer, a laptop computer, a mobile device, a handheld device, a tablet, an iPad, a Kindle, a cellular phone, a smart phone, a personal digital assistant (PDA), a networked television, a networked media player, and a networked digital video recorder (DVR).

In some embodiments, the computer device is connected to a printing or display device, via wireless or wired connection.

In some embodiments, the computer device is connected to a printing or display device, via wireless or wired connection.

In some embodiments, the one or more end products are selected from the group consisting of a pastry, a meat dish, a seafood dish, a fish dish, a salad, a mixed drink, a cocktail, a mocktail, a confectionary type, a dessert, a vegetable dish, and a soup. In some embodiments, the one or more desired characteristics are created based on the end product selected by the user. In some embodiments, the desired characteristic represents a taste, a flavor, a smell, a texture, or a color, or a combination thereof. Again, methods of preparation, or selection and/or navigation via composition frames are applied in any of the embodiments described herein.

In some embodiments, the one or more first ingredients are created based on the desired characteristic selected by the user. In some embodiments, the one or more second ingredients are compatible with the first ingredient selected by the user. In some embodiments, the one or more second ingredients have a compatibility score with the first ingredient that is above a set value. In some embodiments, the one or more second ingredients are created based on the end product selected by the user. In some embodiments, the at least one second ingredient is selected based on the first ingredient selected by the user.

In some embodiments, the one or more third ingredients are created based on the desired characteristic selected by the user. In some embodiments, the at least one third ingredient is selected based on the first or at least one second ingredient selected by the user. In some embodiments, the at least one third ingredient is selected based on the first and at least one second ingredient selected by the user.

One of skill in the art would understand that additional ingredients can be added and the additional ingredients are compatible with the known ingredients.

In some embodiments, the interface is provided by a computer program product.

In some embodiments, the interface is provided by web-based interface, an executable computer program, or a mobile application.

In one aspect, provided herein are a method for providing a food or drink recipe. The method comprises the steps of receiving, from a user via an interface on a computer device, one or more ingredients, where the one or more ingredients are entered by the user or selected by the user using the interface from a plurality of ingredients; receiving, from the user and via the interface, an end characteristic, where the end characteristic is associated with at least one of the one or more ingredients, and where the end characteristic is an end product, a desired characteristic or a combination thereof, each of which being associated with the at least one of the one or more ingredients; and providing, to the user via the interface, a food or drink recipe comprising a quantity for each of the one or more ingredients. Additionally and optionally, the method comprises a step of providing a method of preparation to one or more ingredients, according to the ingredients and their quantities, thereby creating an actual characteristic that approaches the end characteristic.

One of skill in the art would understand that the method of preparation may vary depending on the ingredients and their quantities.

In one aspect, provided herein are a computer program product for use in conjunction with a computer having a processor and a memory connected to the processor, the computer program product comprising a computer readable storage medium having a computer program mechanism encoded thereon, wherein the computer program mechanism may be loaded into the memory of the computer and cause the computer to carry out the method of any one of the embodiments or any combinations thereof.

In one aspect, provided herein are a method for creating a food or drink recipe. The method comprises the steps of selecting, via an interface on a computer device, a type of end product, wherein the end product is selected by the user from one or more end products; selecting, via the interface, a desired characteristic of the end product, wherein the desired characteristic is selected by the user from one or more desired characteristics; selecting, via the interface, a first ingredient appropriate for being used in the end product, wherein the first ingredient is selected by the user from one or more first ingredients appropriate for being used in the end product; and selecting, via the interface, at least one second ingredient, wherein the at least one second ingredient is selected by the user from one or more second ingredients, wherein the at least one second ingredient, when combined with the first ingredient, is suitable for creating an actual characteristic that approaches the desired characteristic. Additionally and optionally, the method comprises the step of selecting, via an interface on a computer device, a method of preparation for each ingredient or a combination thereof and/or the step of selecting a step of selecting a composition frame.

In some embodiments, the method also comprises a step of causing, via the interface, a food or drink recipe to be rendered, wherein the food or drink recipe comprises the first ingredient at a first quantity, the at least one second ingredient at a second quantity and optionally a preparation method.

In some embodiments, the appropriate quantities of the ingredients are determined additionally based on the desired intensity value of an ingredient in the end product.

In one aspect, provided herein is a system for creating a food or drink recipe. The system comprises a database comprising different types of end products and a means for allowing selection of a type of end product, a means for allowing selecting a desired characteristic of the end product, a means for providing a selection of one or more first ingredients appropriate for being used in the selected type of end product, and for allowing selecting one or more of the first ingredients, a means for providing a selection of one or more second ingredients by their compatibilities with the first ingredient, the one or more second ingredients suitable for approaching the desired characteristic, and for allowing selecting one or more of the second ingredients, and a means for calculating quantities of the selected first and second ingredients, the quantities being appropriate for approaching the desired characteristic. Additionally, the system comprises a database comprising different methods of preparation and a means for allowing selection of a method of preparation, a means for allowing selecting a composition frame.

In some embodiments, the means for providing a selection of the one or more second ingredients is adapted for restricting the selection based on the type of end product.

In some embodiments, the means for providing a selection of the one or more second products is adapted for linking the type of end product to a composition frame consisting of a number of ingredient types and for repeating providing a selection and allowing selecting of one or more second ingredients until at least one ingredient is selected for each ingredient type by its compatibility with the first ingredient and/or one or more or all of the already selected second ingredients.

In some embodiments, the means for allowing selecting a desired characteristic is adapted for selecting a taste, a flavor, a smell, a texture, or a color, or a combination thereof.

In some embodiments, the means for allowing selecting a desired characteristic is adapted for selecting a matrix of at least two numerical values.

Upon selecting a type of end product, the cook, consumer, recipe developer or cocktail maker further selects a characteristic he would like to obtain in the end product. Such characteristic may be any type of characteristic a food product can have, such as a taste, a flavor, a smell, a texture, a color, or a combination thereof.

Then a first ingredient is selected that is appropriate for being used in the selected end product. In a corresponding computer implemented method, a list of first ingredients may be automatically provided and the user makes his choice from the list.

Then, by compatibility analysis with the first ingredient, for example by making use of a compatibility scoring or ranking tree from the first ingredient, the user selects a number of second ingredients matching well with the first ingredient and makes a further selection by choosing from these well-matching ingredients an ingredient that is appropriate for approaching the desired characteristic. Alternatively, instead of starting immediate selection by compatibility scoring or ranking, initially ingredients that are appropriate for approaching the desired characteristic may be selected, upon which then subsequently further selection is done by compatibility scoring or ranking. In a corresponding computer implemented method, a list of second ingredients may be automatically provided, which is filtered and/or organized according to their compatibility scores or ranks with the first ingredient. Furthermore this list is filtered and/or organized according to appropriateness for approaching the desired characteristic prior to second ingredient selection. The user selects a number of second ingredients from this list.

The step of selecting a second ingredient may be repeated several times. In a corresponding computer implemented method, the list of selectable second ingredients may be filtered and/or organized according to their compatibility scores or ranks with the first ingredient and/or one or more or all of the already selected second ingredients.

In another embodiment of this invention, the list of selectable ingredients (e.g., for first ingredient, second ingredient, third ingredient and etc.) can be additionally filtered and/or organized according to following characteristics of the ingredients:
  price, profit, margin and/or other commercial properties
  regional origin availability
  seasonality
  desirability
  preference, acquired and innate
  nutritional data
  health factors
  social factors
  environmental factors
  sustainability
  genetics After determining the first and the at least one second ingredient, the appropriate quantities of the first and the at least one second ingredient are calculated in function of the desired characteristic to be approached.

Approaching the desired characteristic may be achieved in different ways: the second ingredients may be used to introduce a characteristic in the recipe which was not present in the first ingredient, or they may be used to weaken or to strengthen a characteristic of the first ingredient. It should be clear, as already stated earlier, that the list of selectable second ingredients, apart from being filtered and/or organized by their compatibility scores or ranks, is subject to further filtering and/or organizing as a function of whether they are capable of introducing a characteristic in the recipe which was not present in the first ingredient or an already selected second ingredient, or whether they are capable of weakening or strengthening a characteristic of the first ingredient or an already selected second ingredient.

A method in accordance with the present invention eliminates the need for resource consuming searches for new ingredient combinations and their respective quantities during recipe development. With the aid of the method it is guaranteed that selected ingredients combine well according to their compatibility scores or ranks and are fit for approaching a selected desired characteristic; their respective quantities are automatically calculated in function of the selected desired characteristic. The method allows for immediate development up to the level of the final recipe and thus avoids trail-and-error recipe development.

Since a method in accordance with the present invention aims to avoid trial-and-error recipe development as much as possible, a first advantage is that a new food or drink recipe may be created with decreased iterative and time-consuming work Secondly, a new food or drink recipe can be created with less waste of ingredients because of the avoidance of resource consuming trial-and-error recipe development.

Further, cooks and cocktail makers can be capable to find combinations of ingredients that are previously unknown.

Other benefits of a method in accordance with the present invention may be that it decrease overstock, and/or optimizes the cost, profit or margin of a recipe, and/or optimizes the nutritional requirements of a recipe, and/or maximizes sustainability of a recipe, and/or maximizes/minimizes the quantity of certain ingredients in a recipe, an/or maximizes health benefits.

In an embodiment of the present invention, the selection of the second product may be restricted based on the end product. In a corresponding computer implemented method a list of second ingredients will be provided selected by their compatibility scores or ranks, by being appropriate for approaching the desired characteristic, and by the level of usability in the selected end product.

In another embodiment of a method in accordance with the present invention, the compatibility scores or ranks is dependent on a cooking technique appropriate for preparing the end product type. Because a compatibility score or rank tree of a target ingredient changes dependent on the cooking technique used for preparing the ingredient, the compatibility tree used for selecting the second ingredient may change depending on the selected type of end product and/or depending on the selected preparation method.

Similarly, a compatibility score or rank tree of an ingredient may change dependent on characteristics like its origin, brand, season of the year, year, and etc. Consequently, the second ingredients may be selected from compatibility score or rank trees taking in account these characteristics.

As already stated above, in the context of the present invention a desired characteristic of the end product may be any type of characteristic a food product can have, such as a taste, a flavor, a smell, a texture, or a color. Such characteristic may be expressed as a value representing an extent of presence of the characteristic in the end product. Examples of such characteristic may be a defined sweetness, fattiness, and the like. In particular in a corresponding computer implemented method, such value representing an extent of presence of the characteristic may be a numerical value within a numerical range from no presence up to overpowering presence.

In some embodiments, The actual characteristic comes from experimental analysis of the end product. Exemplary parameters include but are not limited to sweetness, saltiness, acidity and etc. and each can be varied. For example, saltiness is based on the measurement of the concentration of salt. The relation between concentration of salt and saltiness was determined by an expert panel.

In some embodiments, the parameters reflect the texture of the end product. Examples of parameters for texture include but not limited to the following:
  Creaminess: from water to full fat custard
  Thickness: water to cream
  Airy: water to chocolate mousse In some embodiments, both aroma and taste modalities are used to describe the desired characteristic of end product. In some embodiments, aroma or taste modalities are used to describe the desired characteristic of end product. For example, only the taste modality is used in the desired characteristic for the cocktails.

In some embodiments, for each desired characteristic of an end product the relevant parameters are determined by an expert panel. An expert panel of chefs and bartenders evaluate variations of these parameters in the characteristic A balanced set of parameters results in a desired characteristic for the end product.

In some embodiments, the same characteristic or similar characteristics (e.g., actual, end or calculated characteristics) can result from multiple combinations of parameters and ingredients.

Computing Characteristic

In order to express the presence of a characteristic in an ingredient, a value (preferably a numerical value) may be assigned to each significant characteristic of an ingredient, this characteristic may be a taste, a flavor, a smell, a texture, or a color, or a combination thereof. For example, stevia has a much higher sweetening power value than cane sugar, but also a higher bitterness value. Syrup is more viscous than water, a potato chip is harder than a chocolate chip cookie. Based on these values, the appropriate quantities may be calculated to approach the desired characteristic. The presence of a characteristic in an ingredient may be determined and quantified by chemical and/or physical analysis, or by organoleptic observations.

In some embodiments, the quantities of selected ingredients are calculated by an optimization algorithm that iteratively changes the quantities until the distance between the actual characteristic and the desired characteristic is minimal i.e., optimal.

The appropriate quantities of the ingredients may be determined additionally based on the intensity value of a typical flavor, or smell component in the ingredients. In the context of the present invention, the intensity value of an ingredient is understood as the intensity of the typical taste, flavor, or smell of the ingredient based on which one can identity it. For example, lamb meat has a typical taste and smell with a relatively high intensity value compared to veal meat. Ripened cheeses have a typical taste and smell with relatively high intensity value compared to young cheeses. In an embodiment of this invention the appropriate quantities of the ingredients may be additionally calculated in order that the absolute intensity of each of the ingredients is identical; thus reaching a balance in the recipe where each ingredient may be perceived equally. In the context of this invention, absolute intensity is understood as the intensity of an ingredient multiplied with its quantity.

Alternatively an appropriate quantity of an ingredient may be additionally calculated by approaching its absolute intensity to a predefined desired intensity.

In some embodiments, the selection and calculation of quantity of an ingredient may also be based on its nutritional values, its glycemic index, or other health related characteristics, as mentioned earlier. There is no "one size fits all" optimal diet for individuals, and this has been demonstrated in recent years in studies on gene-diet interactions and the emergence of nutrigenomics. Biometric data from the patient, genetics and patient patterns can also be taken into account for the selection and calculation of quantity of an ingredient.

Systems and Devices

Figure 4A:
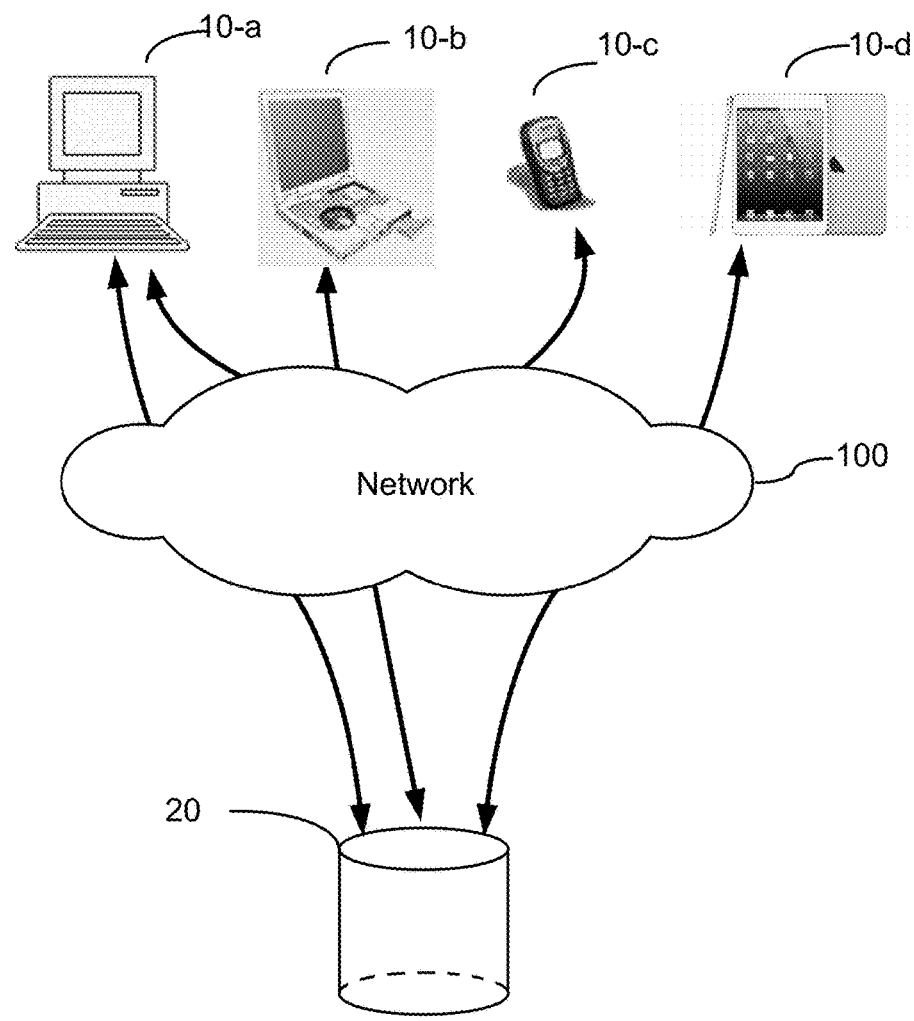
FIGS. 4A-4C illustrate exemplary embodiments in accordance with the invention.

Also provided herein are systems and devices for implementing the methods for creating a food or drink recipe as described herein. As illustrated in FIG. 4A, computer device 10 are connected to a remote data server 20 via network 100. A computer device includes but is not limited to, for example, a networked device, a local device, a desktop computer, a laptop computer, a mobile device, a handheld device, a tablet, an iPad, a Kindle, a cellular phone, a smart phone, a personal digital assistant (PDA), a networked television, a networked media player, or a networked digital video recorder (DVR).

In one aspect, a user can start creating a food or drink recipe, for example, by launching a network-based interface through a host application on the computer device. Computer device 10 connects to a remote server 20 via network 100.

In some embodiments, the host application (e.g., 202 of FIG. 4B) is an embedded application in another program (e.g., as part of a web interface such as a browser). In some embodiments, a host application is a stand-alone program; for example, a mobile app or a dedicated computer program run on a tablet, a laptop or desktop computer. In some embodiments, the user sends one or more keywords (e.g., an end product, a desired characteristic or an ingredient) via the interface. The keywords can be processed by various tools/programs on the remote database (e.g., data processing application 538, network application 546, and customer support tools 548). Processing results, e.g., one or more end products, one or more characteristics, one or more ingredients, one or more cooking/processing techniques, one or more recipes, is sent to computer device 10.

Figure 4B:
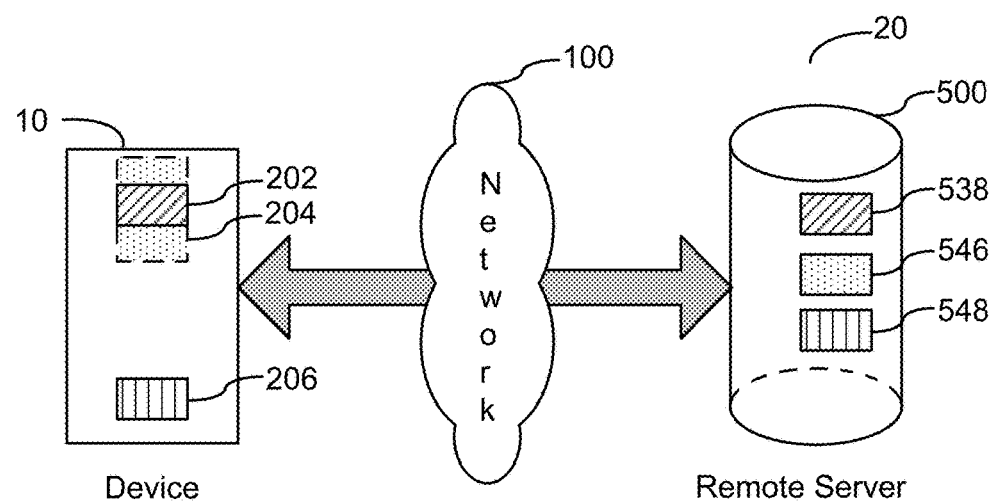
Figure 4C:
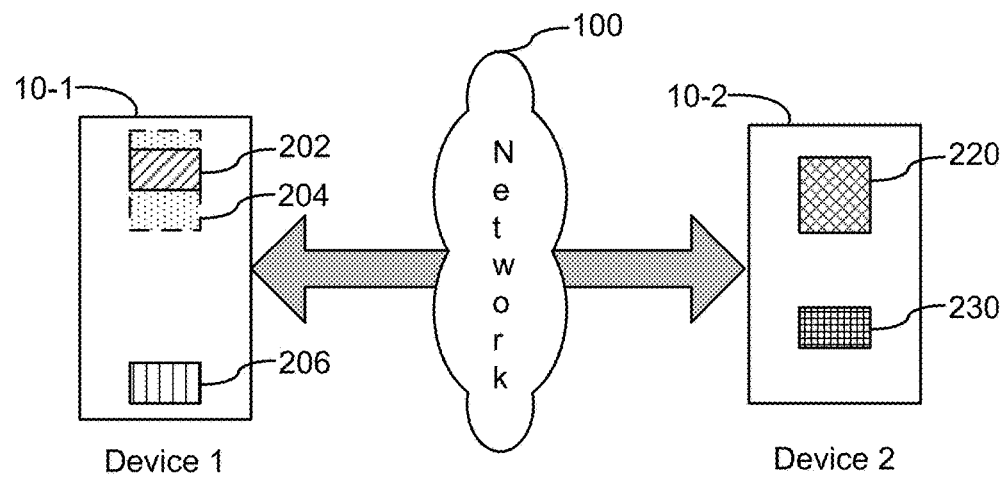
Figure 5:
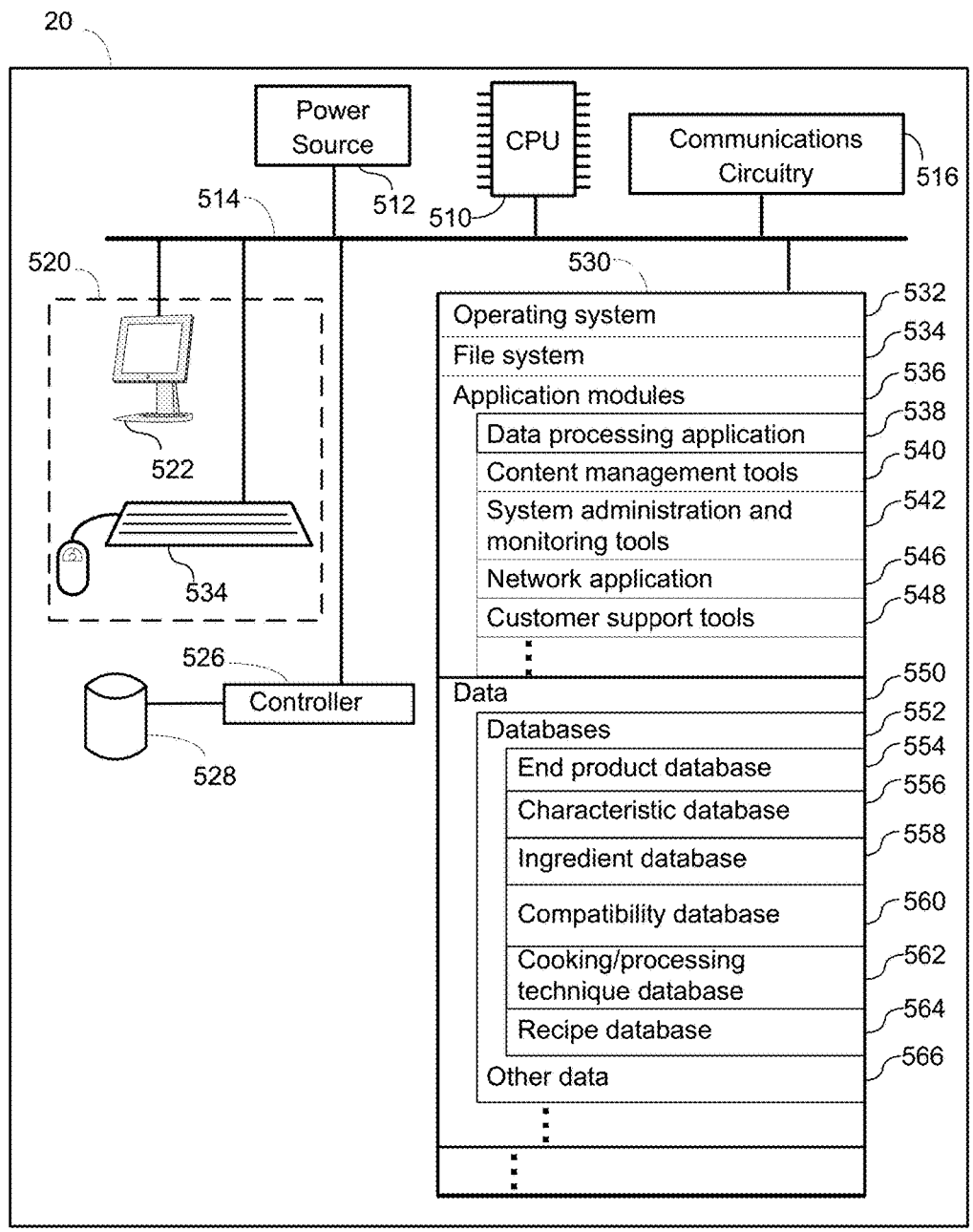
FIG. 5 illustrates an exemplary embodiment in accordance with the invention.

In some embodiments, a network browser, often a web browser, is a software application that enables a user to display and interact with text, images, videos, music and other information typically located on a Web page at a website on the World Wide Web or a local area network. For example, as depicted in FIGS. 4B and 4C, client device 10 comprises a host application 202 that is embedded in a network browser 204 while client device 10 comprises a host application 202. In some embodiments, host application 202 may be an Application Programming Interface (API) or an Application Binary Interface (ABI) application embedded in a network browser 204, for example, Internet Explorer, Mozilla Firefox, Safari, Opera, Opera Mini, Camino, Netscape, or Lynx.

In some embodiments, computer devices 10 are equipped with network capacity (e.g., through a network module 206 as depicted in FIGS. 4B and 4C). In some embodiments, network module 206 allows the client devices to communicate across different network platform.

In some embodiments, computer device 10 connects to another computer device via network 100. For example, one of the computer devices local host of database (e.g., elements 220) and tools (e.g., element 230) for processing keywords and sending results to the other device.

Remote Data Server

In some embodiments, remote data server 20 may comprise a central processing unit 510, a power source 512, a user interface 520, communications circuitry 516, a bus 514, a non-volatile storage controller 526, an optional non-volatile storage 528, and a memory 530.

Memory 530 may comprise volatile and non-volatile storage units, for example random-access memory (RAM), read-only memory (ROM), flash memory and the like. In some embodiments, memory 530 comprises high-speed RAM for storing system control programs, data, and application programs, e.g., programs and data loaded from non-volatile storage 528. It will be appreciated that at any given time, all or a portion of any of the modules or data structures in memory 530 can, in fact, be stored in memory 528.

User interface 520 may comprise one or more input devices 524, e.g., keyboard, key pad, mouse, scroll wheel, and the like, and a display 522 or other output device. A network interface card or other communication circuitry 516 may provide for connection to any wired or wireless communications network 100 (e.g., FIGS. 4A and 4B). Internal bus 514 provides for interconnection of the aforementioned elements of the remote data server 20.

In some embodiments, operation of remote data server 20 is controlled primarily by operating system 532, which is executed by central processing unit 510. Operating system 532 can be stored in system memory 530. In addition to operating system 532, a typical implementation of system memory 530 may include a file system 534 for controlling access to the various files and data structures used by the present invention, one or more application modules 336, and one or more databases or data modules 550.

In some embodiments in accordance with the present invention, applications modules 336 may comprise one or more of the following modules described below and illustrated in FIG. 3.

Data Processing Application 538.

In some embodiments, a data processing application 538 receives and processes content shared between client devices 10 and between a client device 10 and remote data server 20. For example, manually entered or selected data (e.g., end product, desired characteristics, ingredients and etc.) are sent from client devices 10 to remote data server 20 and subsequently stored by remote data server 20.

By applying computation techniques (e.g., hash functions), data processing application 538 turns raw data sent from a client device into digital data to construct one or more databases. For example, most frequently entered ingredients are used to rank and organize ingredients into an ingredient database or a database of ingredient types (e.g., element 558 or 558-a).

In some embodiments, data processing application 538 is used to compute a compatibility score between two ingredients. In some embodiments, data processing application 538 is used to compare and rank compatibility scores from multiple pairs of ingredients. In some embodiments, data processing application 538 is used to compute a characteristic (a desired characteristic or an actual characteristic). In some embodiments, data processing application 538 is used to compute quantities of each ingredient in an end product.

Content Management Tools 540.

In some embodiments, content management tools 540 are used to organize different forms of databases 552 into multiple databases, e.g., an end product database 554, a characteristic database 556, an ingredient database 558, a composition frame database 558-a, an ingredient compatibility database 560, a preparation method database 562, a recipe database 564 and other data 566. In some embodiments in accordance with the present invention, content management tools 540 are used to search and compare any of the databases hosted on remote data server 20. Content in accordance with the present invention may be, for example, a text message, a URL, a web link, a note message, a post message, a file, an image, an audio file, a video file, a flash file, a media file, a slideshow file, any printable file, or any ASCII or binary file or data structure.

The databases stored on remote data server 20 comprise any form of data storage system including, but not limited to, a flat file, a relational database (SQL), and an on-line analytical processing (OLAP) database (MDX and/or variants thereof). In some specific embodiments, the databases are hierarchical OLAP cubes. In some embodiments, the databases each have a star schema that is not stored as a cube but has dimension tables that define hierarchy. Still further, in some embodiments, the databases have hierarchy that is not explicitly broken out in the underlying database or database schema (e.g., dimension tables are not hierarchically arranged). In some embodiments, the databases in fact are not hosted on remote data server 20 but are in fact accessed by centralized data server through a secure network interface. In such embodiments, security measures such as encryption is taken to secure the sensitive information stored in such databases.

In some embodiments, content management tools 540 utilize a chromosome-like system or method for determining data, such as any of those disclosed in U.S. patent application Ser. No. 11/664,710, filed on Oct. 11, 2005, which is hereby incorporated by reference herein in its entirety.

In some embodiments, content management tools 540 utilize a clustering method for determining member/user characteristics.

System Administration and Monitoring Tools 542.

In some embodiments in accordance with the present invention, the system administration and monitoring tools 542 administer and monitor all applications and data files of remote data server 20. System administration and monitoring tools 542 control which servers or devices have access to remote data server 20. In some embodiments, security administration and monitoring is achieved by restricting data download access from remote data server 20 such that the data is protected against malicious access. In some embodiments, system administration and monitoring tools 542 use more than one security measure to protect the data stored on remote data server 20. In some embodiments, a random rotational security system may be applied to safeguard the data stored on remote data server 20. In some embodiments, a user gains access to a database on remote data server 20 using a user account via a password. In such embodiments, a user profile can be established to keep track of the activities of the user and the recipes created by the user.

Network Application 546.

In some embodiments, network applications 546 connect a remote data server 20 to multiple network services. In some embodiments, a remote data server 20 is connected to multiple types of client devices 10, which requires that remote data server 20 be adapted to communication with different types of network interfaces, for example, router based computer network interfaces, switch based phone like network interfaces, and cell tower based cell phone wireless network interfaces. In some embodiments in accordance with the present invention, upon recognition, a network application 546 receives data from intermediary gateway servers before it transfers the data to other application modules such as data processing application 538, content management tools 540, and system administration and monitoring tools 542.

Customer Support Tools 548.

Customer support tools 548 assist users with information or questions regarding their accounts, technical support, billing, and etc. In some embodiments, customer support tools 548 may allow a member to manually input or select the member's interest category to facilitate better characterization of the member's sharing preference profile.

In some embodiments, each of the data structures stored on the remote data server 20 is a single data structure. In other embodiments, any or all such data structures may comprise a plurality of data structures (e.g., databases, files, and archives) that may or may not all be stored on remote data server 20. The one or more data modules 550 may include any number of databases 552 organized into different structures (or other forms of data structures) by content management tools 540.

In addition to the above-identified modules, data 550 may be stored on remote data server 20 or on a computer that is addressable by remote data server (e.g., any computer that the remote data server can send information to and/or retrieve information from). Such data comprises content databases 552 and member data 564. Exemplary databases 552 include, but are not limited to, end product database 554, characteristic database 556, ingredient database 558, compatibility database 560, preparation method dataset 562, and recipe database 564 and other data 566, which are described below in more detail.

End Product Database 554.

In some embodiments, remote data server 20 hosts an end product database 554. End products can be stored according to cuisine, main ingredients, or any feature associated with the end product. In some embodiments, end product database 554 comprises one or more sub-database according to a feature associated with the end product. In some embodiments, end product database 554 is stored on, and managed by, programs of remote data server 20. In some embodiments of the present invention, end product database 554 may be searched by a data processing application 538. In some embodiments of the present invention, end product database 554 may be maintained, updated and managed by content management tools 540. In some embodiments, each time a new end product is inputted by the member, end product database 554 will also be updated accordingly.

Characteristic Database 556.

In some embodiments, remote data server 20 hosts a characteristic database 556. One or more characteristics associated with an end product are organized and stored in characteristic database 556. In some embodiments, a characteristic of an end product represents an overall feature of the end product (e.g., a gravy, a cream, a veggie, a butter and a bordelaise type). In some embodiments, a characteristic of an end product is dominated by a primary ingredient in the end product. In some embodiments, a characteristic of an end product is presented by all ingredients in the end product.

Ingredient Database 558.

In some embodiments, remote data server 20 hosts an ingredient database 558. One or more characteristics associated with an end product are organized and stored in ingredient database 558. In some embodiments, ingredient data 558 are organized by types of food or drink.

Composition Frame Database 558-*a:*

In some embodiments, remote data server 20 hosts a composition frame database 558-*a*. Composition frame database 558-*a* can be part of ingredient database 558 or as a separate database. A composition frame comprises one or more ingredient types, through which a user can select or navigate among different ingredients.

Compatibility Database 560.

In some embodiments, remote data server 20 hosts a compatibility database 560. One or more compatibility scores associated with an end product are organized and stored in a compatibility database 560. In some embodiments, compatibility between food or drink ingredients is determined by individual components in connection with each ingredient. In some embodiments, individual components from a pair of ingredients are compared before a compatibility score is calculated. In some embodiments, compatibility database 560 comprises one or more matrices of compatibility scores for computing a compatibility score of an ingredient pair. In some embodiments, a compatibility score is calculated based on one or more primary components of an ingredient. In some embodiments, a compatibility score is calculated based on all components that are considered relevant in an ingredient.

Preparation Method Database 562.

In some embodiments, a preparation method database 562 is stored on remote data server 20. Methods of preparation include but are not limited to methods of cooking, processing, assembling, making, and etc. In some embodiments, a cooking or processing technique is used to modify a compatibility score, for example, by enhancing or reducing the effects of a component in an ingredient. Because compatibility scores contributes to the overall feature of an end product (e.g., a desire characteristic), applying one or more cooking/processing techniques to one or more ingredient can ultimately alter a desired characteristic of the end product. Exemplary preparation methods include but are not limited to being shaken, being stirred, gassing, de-gassing baking, frying, steaming, roasting, hot processing, cold processing, marinating, salting, curing, pureeing, chopping, kneading, blending, grinding, poaching and etc.

Recipe Database 564.

In some embodiments, a recipe database 564 is stored on remote data server 20. In some embodiments, recipes created by users are stored in recipe database 564. In some embodiments, the recipes are organized by food types, drink types, cuisine types, cooking techniques, processing types, and ingredient types. A user can choose to access recipes created by the user in the past. A user can also choose to share recipes with other users through a community-based sharing interface, e.g., by customer support tools 548.

In addition, as another embodiment according to the present invention, a system for creating a new food or drink recipe is provided comprising one or more of the following:

a database comprising different types of end products and
  a means for allowing selection of a type of end product,
a means for allowing a selection of a desired characteristic
  of the end product,
a means for providing a selection of one or more first
  ingredients appropriate for being used in the selected
  type of end product, and for allowing selecting one or
  more of the first ingredients,
a means for providing a selection of one or more second
  ingredients by their compatibility scores or ranks with
  the first ingredient, the one or more second ingredients
  suitable for approaching the characteristic, and for
  allowing selecting one or more of the second ingredients,
a means for allowing a selection of a preparation method
  for one or more ingredients of the end product,
a means for providing a composition frame,
a means for calculating quantities of the selected first and
  second ingredients, the quantities being appropriate for
  approaching the desired characteristic.

Preferably, the means for providing a selection of one or more second ingredients by their compatibility scores or ranks with the first ingredient comprises a database of compatibility score or rank trees or a list with matching ingredients and match values In an embodiment, the means for providing a selection of the one or more second products is adapted for restricting the selection based on the type of end product.

In another embodiment, the means for providing a selection of the one or more second products is adapted for linking the type of end product to a composition frame consisting of a number of ingredient types and for repeating providing a selection and allowing selecting of one or more second ingredients until at least one ingredient is selected for each ingredient type present in the composition frame.

Alternatively, the means for providing a selection of the one or more second ingredients is adapted for selecting second ingredients without making use of composition frames. Indeed, selecting second ingredients is also done based on compatibility scores or ranks combined with iterative calculation of what ingredients are most suitable for approaching the desired characteristic. In addition, iterative calculation can also provide whether the already selected second ingredients and their characteristics suffice for adequately converging to the desired characteristic of the end product.

Further, the means for providing a selection of one or more second ingredients may be adapted for selecting by compatibility score or rank dependent on a cooking technique appropriate for preparing the end product type.

The means for allowing selecting a desired characteristic may be adapted for selecting a taste, a flavor, a smell, a texture, or a color, or a combination thereof.

In particular, selecting a value of sweetness, sourness, saltiness, bitterness, umami, pungency, coolness, numbness, astringency, metallicness, fattiness, heartiness and the like, or a combination thereof may be provided Also selecting a value of dryness, crumbliness, crispiness, crunchiness, brittleness, graininess, gumminess, hardness, moisture release, mouthcoating, slipperiness, smoothness, homogeneity, viscosity, or a combination thereof may be provided.

In a particular embodiment, a system may be provided wherein the means for allowing selecting a desired characteristic is adapted for selecting a matrix of at least two of values.

In a further embodiment, the means for calculating appropriate quantities may be adapted for additionally calculating the appropriate quantities based on the desired intensity of an ingredient in the end product.

The means for providing a selection of the one or more second ingredients may be adapted for additionally restricting the selection based on physical and/or technical requirements corresponding to a cooking formulation.

Additionally and optionally, provided herein is a means for permitting a selection of a method of preparation, by which one or more ingredients can be prepared. The preparation method can be applied to any ingredient (e.g., first ingredient, second ingredient, third ingredient, and etc.). Further optionally, provided herein is a means for permitting a selection of composition frame, through which a user selects and navigates among different ingredient types.

For example, in some embodiments, a method can be provided wherein the selection of the second ingredient suitable for approaching the characteristic is additionally restricted based on physical and/or technical requirements corresponding to a cooking formulation. Depending on the selected type of end product and its composition frame, the ingredients within an ingredient type may be restricted. For example, in case fats are required in the composition frame, the selection can be restricted to butters excluding oils. In some embodiments, a method may be provided wherein the appropriate quantities are additionally calculated based on physical and/or technical requirements corresponding to a cooking formulation. Depending on the selected type of end product and its composition frame, the quantitative ratios between the different ingredients may be restricted to usable ranges.

In addition, the means for calculating appropriate quantities may be adapted for calculating the appropriate quantities additionally based on physical and/or technical requirements corresponding to a cooking formulation.

In a particular embodiment according to the present invention, a system for creating a new food or drink recipe may be provided wherein the means for providing a selection of one or more first ingredients is adapted for selecting the one or more first ingredients by its compatibility score or rank with an ingredient, preferably the main ingredient, of an already created food or drink recipe.

Additionally, the means for providing a selection of one or more second ingredients may be adapted for determining the characteristic of the end product to be approached by balancing the characteristic of an already created food or drink recipe.

A method or a computer implemented method or a system according to any of the above embodiments may be used for driving automatic drink machines, automatic cocktail machines, automatic food preparation equipment, and the like.

A method or a computer implemented method or a system according to any of the above embodiments may be linked to patient metrics to optimize health or lifestyle, to consumer preferences from consumer metrics to increase liking, to details from retailers to reduce the overstock or increase margin, to availability of ingredients or to selected ingredients to reduce waste.

Additional Exemplary Applications

The concepts of matching ingredients can expand various business models to another dimension; including but not limited to e.g., web search, retail, nutrition, restaurant, bar, lounge, e-commerce, household, and etc. Methods in accordance with the present inventions are used but not limited in the following exemplary applications:

1. Connect Advertisements of Matching Ingredients to Search Engine Results:

Traditionally, vendors of the direct query products bid for advertisement positions in connection with the query products. Based on matching ingredients, vendors of products that match or are compatible with the query product can also bid for advertisement positions in connection with the query products, as illustrated below.

a. Next to the results from a search engine, advertisements of ingredients matching the query ingredient are published. If e.g., strawberry is searched in a search engine, advertisements of e.g., a chocolate brand matching the strawberry can appear. Vendors of the chocolate brand can bid on each click they receive (CPC: Cost per Click pricing model) and can bid on keywords that are relevant to their products/business.

Based on the match between strawberry and the chocolate brand, a recipe can be generated. When a type of dish is mentioned like 'strawberry ice-cream', an ice-cream recipe with strawberry and the chocolate brand will be generated.

If a consumer searched for "Potato" and the search result had a compatibility recipe twist in the search results that included "Tomato," additional advertising opportunities become available. For example, a company selling tomato products could bid on the link for Tomato.

b. Next to the recipe results from a search engine, a drink suggestion can be added. Based on the ingredients and quantities of the recipe, a drink or an extra ingredient can be suggested and will appear as an advertisement.

For example, if a consumer searched "Tomato," the search result can have a compatible beverage that is sponsored by the vendor of the beverage.

c. When a combination of ingredients is added to the search engine, a new recipe can be created including ingredients of brands that paid for advertisements and fit to the ingredients. Compatibility content provides search engines with increased keyword inventory and the opportunity to increase revenue from advertising.

2. Optimization of Restricted Diets (e.g., Type 2 Diabetes Diets)

When a diabetes patient is diagnosed, a doctor provides caloric and macronutrient recommendations but such recommendations are abstract to the average individual. Studies show diet-related changes work best when introduced slowly. The combination of abstract recommendations and drastic dietary changes is low compliance. A method in accordance with the present invention can teach patients to gradually remove certain foods from their diets while incorporation better, healthier choices. These recipes will take patient metrics into consideration, thereby serving as a self-teaching tool for patients.

3. Optimization of Diets for Athletes (e.g., Carbohydrate Loading Plan)

Days prior to endurance competition, sportsmen start to load carbohydrates to maximize muscle glycogen stores. Large quantities of carbohydrates have to be eaten: 9 g per kg body weight. This big amount of carbohydrates can only be eaten when proteins or fats (giving satiety) are prevented.

A method in accordance with the present invention can generate a broad range of recipes taken into account what the sportsmen prefer and are carbohydrates. In that way more variation can be added to the diet.

4. Menu Card with Drink or Food Suggestions

A chef or bartender can uploaded his recipes. The recipe engine can present drinks or side dishes fitting the uploaded recipes. Drinks can be beer or wine or can also be cocktails generated through a method in accordance with the present invention. Side dishes can be bar foods or food items like salads, cereals, and etc.

Results of the matches can be published in a digital or offline menu.

5. Optimization Overstock Retail

When a retailer has too much stock of a certain product or a chef bought too much of a certain ingredient, the product can be indicated into a method in accordance with the present invention. All ingredients and applications fitting this product in overstock, can be integrated into recipes for the consumers.

6. Optimize Food or Drink Suggestion E-Commerce

When buying grocery or food online, a method in accordance with the present invention can generate recipes based on the ingredients a user have bought. Once a user selects a generated recipe, he can offer a drink matching this selection.

7. Custom Drink

Based on the type of cocktail, coffee, tea, juice, soft drink, etc. a person likes and the ingredients he prefers, a method in accordance with the present invention can make a drink recipe fitting your requirements. In case not all ingredients are available, such method could calculate how to obtain your selected flavor profile by making combinations of other not selected ingredients.

The drink recipe is made by e.g., automatic coffee machine online connected.

8. 3D

A method in accordance with the present invention will be able to generate custom recipes taking into account the limitations of the 3D printer 9. iPad to Printer for Cocktail Recipe.

In a cocktail bar, a method in accordance with the present invention allows people to make their own drink by selecting the ingredients they like (and the bar has available). The recipe is automatically printed or send to the bartender, who can make instant the cocktail. Price can also be calculated.

10. Kitchen Device: Balance and Camera

When a consumer or a chef makes a dish, quantities added can vary while following the recipe e.g., too much salt, not enough egg white, and etc. can be added by accident. By combining cameras and balances, a clear view can be obtained of how much of each ingredient is added.

During the preparation and cooking process, a method in accordance with the present invention can recalculate the amount of the other ingredients, so a user still obtains a standard result. This prevents waste of food material and resources.

11. Linking to Database of Recipes

Existing recipes within the database of food companies can be linked to a method in accordance with the present invention. Per region a different composition frame can be used. Through a method in accordance with the present invention the company can generate new line extensions or find combo deals within its product range.

12. Sales Tool

A method in accordance with the present invention can take the role of development chef. When a sales person visit a company to present his products a method in accordance with the present invention can instant develop recipes taking several constraints into account as available other ingredients, cost, skills, . . . .

13. Branding Tool

Consumers can be a part of the product development process. A method in accordance with the present invention can support the consumers by proposing ingredients or making/correcting the recipe. E.g. if a brand wants to create a new type of chips, a method in accordance with the present invention will support the consumer in creating a new flavor.

14. Smart Fridge

Based on the ingredients in the fridge, a method in accordance with the present invention can create recipes.

15. Image Recognition Item in Shopping Basket

While shopping, a shopping basket (or other device) could recognize what is in your basket. By linking to the personal information of the consumer (what the consumer likes/often buys). Based on this information, recipes can be made or suggestions for other foods or drinks.

EXAMPLES

Example 1

Step 1: End Product Type Selection

| End product types |
|---|
| Sauces |
| Cocktails |
| Mocktails |
| Ice creams |
| Mousses |
| Chocolate confections |
| Pizzas |

Step 2: Desired Characteristic of the End Product

| End product characteristics |
|---|
| Martini style |
| Manhattan style |
| Long drink style |
| Sweet & Sour style |
| Bitter & Sweet style |

With predefined composition frame:
1. Liqueur
2. Spirit
3. Acid
4. garnish

Step 3: First Ingredient Selection

According to composition frame, first ingredient must belong to ingredient type Liqueur"

| Liqueur |
|---|
| anisette |
| apricot brandy |
| cherry brandy |
| coffee liqueur |
| Cointreau ® |
| creme de cacao |
| creme de cassis |
| creme de menthe |
| creme de vanilla |
| Crème de banana |
| Crème de cacao |
| Crème de cassis |
| Crème de menthe |
| Curaçao |
| DOM Benedictine ® |
| green chartreuse |
| Mandarine Napoléon |
| Maraschino |
| Orange curacao |

-continued

| Liqueur |
|---|
| Parfait d'amour |
| Passoã ® |
| Peachtree |
| Port |
| sweet vermouth |
| Triple sec |
| yellow chartreuse |

Step 4: Second Ingredient Selection

According to composition frame, second ingredient must belong to ingredient type "Spirit". The ingredients belonging to ingredients type "Spirit" are additionally filtered and ranked according to their compatibility match with the selected first ingredient "Triple sec".

| Spirit |
|---|
| Gin |
| light Rum |
| Dark Rum |
| Bourbon whiskey |
| Rye Whisky |
| Scotch whisky |
| Tequila |
| Brandy |
| Cachaça |
| Pisco |
| Cognac |
| Vodka |
| Calvados |

Step 5: Third Ingredient Selection

According to composition frame, third ingredient must belong to ingredient type "Acid" The ingredients belonging to ingredients type "Acid" are additionally filtered and ranked according to their compatibility match with the selected first ingredient AND second ingredient "Triple sec" and Gin.

| Acid |
|---|
| Lemon juice |
| Lime juice |

Step 6: Fourth Ingredient Selection

According to composition frame, fourth ingredient must belong to ingredient type "garnish". The ingredients belonging to ingredients type "garnish" are additionally filtered and ranked according to their compatibility match with the previous selected ingredients.

| Garnish |
|---|
| Mandarin - fresh |
| Lime peel |
| Carrot - fresh |
| Black pepper - dried |
| Grapefruit - fresh |
| Blueberry - fresh |
| Mint |
| Ginger - fresh |
| Juniper berry - dried |
| Cumin - dried |
| Cardamom - dried |
| Bell pepper - fresh |
| Bergamot - fresh |

-continued

| Garnish |
| --- |
| Common Mango |
| Orange peel |
| Thyme |
| Nutmeg |
| Blackcurrant - fresh |
| Lychee - fresh |
| Rosemary |
| Cilantro - fresh |
| Yuzu |
| Cinnamon - dried |
| Star anise |
| Lemon zest |
| Grapefruit peel |
| Guava - fresh |
| Passion fruit - fresh |
| Lavender - fresh |
| Raspberry - fresh |
| Sage |

Calculation

Quantities of ingredients for approaching the characteristic are obtained by constructing an optimization problem. Since the garnish is a structural different phase and does not contribute to the desired characteristic, it is omitted from the optimization problem. The quantity of the garnish may be calculated by approaching a predefined intensity value with the garnish's intrinsic intensity x its quantity.

| Selection | | Tex1 | Tex2 | Taste1 | Taste2 | Taste3 |
| --- | --- | --- | --- | --- | --- | --- |
| Ingredient 1 | Triple Sec | 32.00 | 33.50 | 32.13 | 2.65 | 0.00 |
| Ingredient 2 | Gin | 31.00 | 66.40 | 0.00 | 0.00 | 0.00 |
| Ingredient 3 | Lemon juice | 0.00 | 88.00 | 4.20 | 47.60 | 0.00 |

The desired characteristic takes a preparation method into account and may be mathematically transformed according to a user selected preparation method. In the case of this example, the preparation method is "shaken".

| | Tex1 | Tex2 | Taste1 | Taste2 | Taste3 |
| --- | --- | --- | --- | --- | --- |
| Desired characteristic of end product AFTER PREPARATION | 13.00 | 77.00 | 7.00 | 6.40 | 0.00 |
| Desired characteristic of end product BEFORE PREPARATION | 21.58 | 61.82 | 11.62 | 10.62 | 0.00 |

The quantities of selected ingredients are calculated by an optimization algorithm that iteratively changes the quantities until the distance between the actual characteristic and the desired characteristic is minimal i.e., optimal. A minimal distance of 2.91 is obtained.

| Selection | | Proportion |
| --- | --- | --- |
| Ingredient 1 | Triple Sec | 0.31 |
| Ingredient 2 | Gin | 0.45 |
| Ingredient 3 | Lemon juice | 0.24 |
| Ingredient 4 | Mint | omitted |

With these proportions, following characteristic of end product is obtained:

| | Tex1 | Tex2 | Taste1 | Taste2 | Taste3 |
| --- | --- | --- | --- | --- | --- |
| obtained characteristic of end product | 23.82 | 61.41 | 10.99 | 12.32 | 0.00 |
| Desired characteristic of end product | 21.58 | 61.82 | 11.62 | 10.62 | 0.00 |

With a Euclidean distance to the desired characteristic of 2.91, volumetric conversion and resealing to a predefined cocktail volume gives:

| Selection | | Quantities |
| --- | --- | --- |
| Ingredient 1 | Triple Sec | 25.49 ml |
| Ingredient 2 | Gin | 43.17 ml |
| Ingredient 3 | Lemon juice | 21.50 ml |

Final quantities may be transformed according to selected end volume and rounded. Calculating Garnish quantity The quantity of the garnish may be calculated by approaching a predefined intensity value with the garnish's intrinsic intensity×its quantity.

Predefined intensity value: 10
Intrinsic intensity value of "Mint": 1/g $$\text{Quantity} = \frac{\text{Predefined intensity value}}{\text{Intrinsic intensity value}}$$

$$\text{Quantity} = \frac{10}{1} g$$

10 g of Mint should be added as garnish to reach the predefined intensity value.

Example 2

Step 1: End Product Type Selection

| End product types |
| --- |
| Sauces |
| Cocktails |
| Mocktails |
| Ice creams |
| Mousses |
| Chocolate confections |
| Pizzas |

Step 2: Desired Characteristic of the End Product

| End product characteristics |
| --- |
| Martini style |
| Manhattan style |
| Long drink style |
| Sweet & Sour style |
| Bitter & Sweet style | composition frame:
1. Spirit
2. cordial
3. Acid
4. Mixer

Step 3: First Ingredient Selection

According to composition frame, first ingredient must belong to ingredient type "Spirit":

| Spirit |
| --- |
| Bourbon whiskey |
| Brandy |
| Cachaça |
| Calvados |
| Cognac |
| Dark Rum |
| Gin |
| light Rum |
| Pisco |
| Rye Whisky |
| Scotch whisky |
| Tequila |
| Vodka |

Step 4: Second Ingredient Selection

According to composition frame, second ingredient must belong to ingredient type "cordial". The ingredients belonging to ingredients type "cordial" are additionally filtered and ranked according to their compatibility match with the selected first ingredient "Vodka".

| Cordial |
| --- |
| elderflower cordial |
| ginger cordial |
| Sugar |
| Grenadine |
| Honey |
| orgeat syrup |
| guava nectar |
| Falernum |

Step 5: Third Ingredient Selection

According to composition frame, third ingredient must belong to ingredient type "Acid" The ingredients belonging to ingredients type "Acid" are additionally filtered and ranked according to their compatibility match with the selected first ingredient AND second ingredient "Vodka" and "elderflower cordial".

| Spirit |
| --- |
| Lime juice |
| Lemon juice |

Step 6: Fourth Ingredient Selection

According to composition frame, Fourth ingredient must belong to ingredient type "Mixer". The ingredients belonging to ingredients type "Mixer" are additionally filtered and ranked according to their compatibility match with the selected first, second and third ingredient "Vodka", "elderflower cordial" and "lime juice".

| Mixer |
| --- |
| peach juice |
| orange juice |
| Tonic |
| lemon-lime soda |
| Lemonade |
| Cola |
| orange flower water |
| passion fruit juice |
| Cider |
| grapefruit juice |
| strawberry juice |
| ginger ale |
| cranberry juice |
| ginger beer |
| apple juice |
| Champagne |
| raspberry juice |
| pineapple juice |
| Prosecco |
| Beer |
| red wine |
| tomato juice |
| Coffee |
| cucumber juice |
| mango nectar |
| pear juice |
| soda water |
| Water |
| white wine |

Step 7: Fifth Ingredient Selection

A garnish can be selected analogously.

| Selection | | Tex1 | Tex2 | Taste1 | Taste2 | Taste3 |
| --- | --- | --- | --- | --- | --- | --- |
| Ingredient 1 | Vodka | 31.00 | 66.40 | 0.00 | 0.00 | 0.00 |
| Ingredient 2 | Elderflower syrup | 0.00 | 51.30 | 44.59 | 0.00 | 0.00 |
| Ingredient 3 | Lime juice | 0.00 | 89.40 | 1.15 | 47.60 | 0.00 |
| Ingredient 4 | Soda | 0.00 | 99.00 | 0.00 | 1.00 | 0.00 |

Preparation method: built

| | Tex1 | Tex2 | Taste1 | Taste2 | Taste3 |
| --- | --- | --- | --- | --- | --- |
| Desired characteristic of end product AFTER PREPARATION | 4.76 | 89.49 | 3.90 | 5.57 | 0.00 |
| Desired characteristic of end product BEFORE PREPARATION | 7.90 | 82.55 | 6.47 | 9.24 | 0.00 |

| Selection | | Proportion |
| --- | --- | --- |
| Ingredient 1 | Vodka | 0.26 |
| Ingredient 2 | Elderflower syrup | 0.14 |
| Ingredient 3 | Lime juice | 0.16 |
| Ingredient 4 | Soda | 0.44 |

| | Tex1 | TEX2 | Taste1 | Taste2 | Taste3 |
| --- | --- | --- | --- | --- | --- |
| obtained characteristic of end product | 7.99 | 82.64 | 6.56 | 9.26 | 0.00 |
| Desired characteristic of end product | 7.90 | 82.55 | 6.47 | 9.24 | 0.00 |

Euclidean distance: 0.16

Volumetric conversion and rescaling to a desired volume

| Selection | | Quantities |
| --- | --- | --- |
| Ingredient 1 | Vodka | 48.07 ml |
| Ingredient 2 | Elderflower syrup | 18.91 ml |
| Ingredient 3 | Lime juice | 27.65 ml |
| Ingredient 4 | Soda | 77.32 ml |

Example 3A

Step 1: End Product Type Selection

| End product types |
|---|
| Sauces |
| Cocktails |
| Mocktails |
| Ice creams |
| Mousses |
| Chocolate confections |
| Pizzas |

Step 2: Desired Characteristic of the End Product

| End product characteristics |
|---|
| Moldable type |
| Slab type |
| Viscous type |
| Hard type |

Step 3: Composition Frame Selection

| Composition frame |
|---|
| Cream based |
| Fruit based |
| Water based |
| Alcohol based |
| Nut based |

Composition frame:
1. Chocolate
2. Dairy product (predefined: butter)
3. Fruit product
4. Sweetener (predefined: sugar)
5. Flavoring User may select according to method above (guided by compatibility matching and ranking) 1 ingredient for ingredient types: chocolate, fruit product and flavoring. Since the flavoring does not contribute to the desired characteristic, it is omitted from the optimization problem. In this case, there is only 1 constant preparation method, the desired characteristic should consequently not be transformed. The quantity of the flavoring can be calculated by approaching a predefined intensity value with the flavoring's intrinsic intensity.

| Selection | | Tex1 | Tex2 | Taste1 | Tex3 |
|---|---|---|---|---|---|
| Ingredient 1 | Dark chocolate 60% | 40.75 | 5.2 | 43.4 | 0.85 |
| Ingredient 2 | Butter | 0 | 83 | 0 | 16.5 |
| Ingredient 3 | Passion fruit puree | 0 | 0.4 | 10.7 | 88.4 |
| Ingredient 4 | Sugar | 0 | 0 | 100 | 0 |

| Selection | | Proportion |
|---|---|---|
| Ingredient 1 | Dark chocolate 60% | 0.464 |
| Ingredient 2 | Butter | 0.216 |
| Ingredient 3 | Passion fruit puree | 0.156 |
| Ingredient 4 | Sugar | 0.164 |

| | Tex1 | Tex2 | Taste1 | Tex3 |
|---|---|---|---|---|
| obtained characteristic of end product | 18.89 | 20.39 | 38.23 | 17.76 |
| Desired characteristic of end product | 18.82 | 20.33 | 38.17 | 17.70 |

Euclidian distance: 2.64

Resealing to a desired end mass

| Selection | | Quantities |
|---|---|---|
| Ingredient 1 | Dark chocolate 60% | 200 g |
| Ingredient 2 | Butter | 93.10 g |
| Ingredient 3 | Passion fruit puree | 67.24 g |
| Ingredient 4 | Sugar | 70.68 g |
| Ingredient 5 | Ginger | 20.22 g |

Example 3B

Multiple ingredients for 1 ingredient type
End product types: chocolate confection
End product characteristics: Slab type
Composition frame: fruit based

| Selection | | Tex1 | Tex2 | Taste1 | Tex3 |
|---|---|---|---|---|---|
| Ingredient 1 | Dark chocolate 60% | 40.75 | 5.2 | 43.4 | 0.85 |
| Ingredient 2 | Butter | 0 | 83 | 0 | 16.5 |
| Ingredient 3.1 | Passion fruit puree | 0 | 0.4 | 10.7 | 88.4 |
| Ingredient 3.2 | Peach puree | 0 | 0.7 | 23.4 | 72.9 |
| Ingredient 4 | Sugar | 0 | 0 | 100 | 0 |

Quantity of the additional fruit product may if necessary (in cause of initial zero solution) be calculated by assuming that (quantity×intensity) of each selected ingredients within a single ingredient type should be equal to each other.

Following constraint was added to the optimization problem:

$$\frac{\text{Quantity}_{passion\ fruit\ puree} * \text{intrinsic Intensity}_{passion\ fruit\ puree}}{\text{Quantity}_{peach\ puree} * \text{intrinsic Intensity}_{peach\ puree}} = 1$$

intrinsic Intensity "passion fruit puree"=5/g
intrinsic Intensity "peach puree"=3/g

| Selection | | Proportion |
|---|---|---|
| Ingredient 1 | Dark chocolate 60% | 0.461 |
| Ingredient 2 | Butter | 0.214 |
| Ingredient 3.1 | Passion fruit puree | 0.065 |
| Ingredient 3.2 | Peach puree | 0.109 |
| Ingredient 4 | Sugar | 0.148 |

| | Tex1 | Tex2 | Taste1 | Tex3 |
|---|---|---|---|---|
| obtained characteristic of end product | 18.81 | 20.33 | 38.17 | 17.70 |
| Desired characteristic of end product | 18.82 | 20.33 | 38.17 | 17.70 |

Euclidian distance: 0.014

Rescaling to a desired end mass

| Selection | | Quantities |
|---|---|---|
| Ingredient 1 | Dark chocolate 60% | 200 g |
| Ingredient 2 | Butter | 92.84 g |
| Ingredient 3.1 | Passion fruit puree | 28.19 g |
| Ingredient 3.2 | Peach puree | 47.28 g |
| Ingredient 4 | Sugar | 64.20 g |
| Ingredient 5 | Ginger | 20.22 g |

Example 4

Same characteristic, different composition frame
End product types: chocolate confection
End product characteristics: Slab type
Composition frame: nut based
Composition frame:
1. Chocolate
2. Dairy product (predefined: butter and cream)
3. nut product
4. Sweetener (predefined: sugar)
5. Flavoring

| Selection | | Tex1 | Tex2 | Taste1 | Tex3 |
|---|---|---|---|---|---|
| Ingredient 1 | Dark chocolate 60% | 40.75 | 5.2 | 43.4 | 0.85 |
| Ingredient 2.1 | Butter | 0 | 83 | 0 | 16.5 |
| Ingredient 2.2 | Cream | 0 | 38 | 3 | 57 |
| Ingredient 3 | Raw almond puree | 0 | 27.74 | 47.81 | 14.08 |
| Ingredient 4 | Sugar | 0 | 0 | 100 | 0 |

| Selection | | Proportion |
|---|---|---|
| Ingredient 1 | Dark chocolate 60% | 0.4429 |
| Ingredient 2.1 | Butter | 0.0000 |
| Ingredient 2.2 | Cream | 0.1966 |
| Ingredient 3 | Raw almond puree | 0.3605 |
| Ingredient 4 | Sugar | 0.0000 |

In this case it is not desirable to fix the zero solution since butter and sugar do not contribute heavily and the final flavor of the end product, furthermore, these products were predefined (i.e., not chosen) by user and are needed functionally to approach the desired characteristic of the end product

| | Tex1 | Tex2 | Taste1 | Tex3 |
|---|---|---|---|---|
| obtained characteristic of end product | 18.05 | 19.77 | 37.05 | 16.66 |
| Desired characteristic of end product | 18.82 | 20.33 | 38.17 | 17.70 |

Euclidian distance: 3.49

Rescaling to a desired end mass

| Selection | | Quantities |
|---|---|---|
| Ingredient 1 | Dark chocolate 60% | 200 g |
| Ingredient 2.1 | Butter | 0 g |
| Ingredient 2.2 | Cream | 88.77 g |
| Ingredient 3 | Raw almond | 162.79 g |
| Ingredient 4 | Sugar | 0 g |

Example 5

Step 1: End Product Type Selection

| End product types |
|---|
| Sauces |
| Cocktails |
| Mocktails |
| Ice creams |
| Mousses |
| Chocolate confections |
| Pizzas |

Step 1b: Matching Ingredient Selection

A product may be selected to which the sauce is to be matched. In following selection steps ingredients will be filtered and ranked according to the compatibility match to the selected ingredients

| Matching ingredients |
|---|
| Beef - grilled |
| bone marrow - roasted |
| Bulgogi - Korea |
| Lamb - roasted |
| Mutton - cooked |
| Pork loin - fried |
| Rabbit |
| Beef 'Angus Aberdeen' - cooked |
| Beijing duck - roasted - China |
| Chicken - cooked |
| Pigeon - roasted - Anjou |
| Turkey - boiled |
| Mackerel - fresh |
| Mitten crab - cooked - China |
| Mussel - cooked |
| Pink salmon - cooked - Organic farmed |
| Pollock - cooked |
| Rainbow trout |
| Redfish |
| Sardine - salted |
| Scallop - cooked |
| Sea bream |
| Shrimp - fresh |
| Shrimp - roasted |

Step 2: Desired Characteristic of the End Product

| End product characteristics |
|---|
| Gravy type |
| Creamed type |
| Bordelaise type |
| Veggie type |
| Butter type |

With predefined composition frame:
1. Fonds
2. Vegetables
3. Deglazing Liquids
4. Herbs Step 3: First Ingredient Selection According to composition frame, first ingredient must belong to ingredient type "Fonds." The ingredients belonging to ingredients type "Fonds" are additionally filtered and ranked according to their compatibility match with the selected matching ingredient "Rainbow trout".

| Fonds |
| --- |
| Shellfish fumet |
| Vegetable stock |
| Chicken stock |
| Veal stock |
| Beef stock |

Step 4: Second Ingredient Selection

According to composition frame, second ingredient must belong to ingredient type "Vegetables." The ingredients belonging to ingredients type "Vegetables" are additionally filtered and ranked according to their compatibility match with the selected matching ingredient AND first ingredient.

| Vegetable |
| --- |
| Beetroot - cooked |
| Broccoli - cooked |
| Eggplant - cooked - Italy |
| Parsley root - fresh |
| Parsnip - fresh |
| Turnip - fresh |
| Celery leaves - fresh |
| Leek - cooked |
| Carrot - fresh |
| Onion - fresh |
| Pumpkin - cooked |
| Cabbage |
| Garlic - fresh |
| Shallot - baked |
| Radish - fresh |
| Fava bean - cooked |
| Beetroot - fresh |
| Cauliflower - cooked |
| Rhubarb - fresh |
| Kale - fresh |
| Kimchi - Korea |
| Celery root - cooked |
| Salsify - cooked |
| Brussels sprouts - fresh |
| Kohlrabi - baked |

Step 5: Third Ingredient Selection

According to composition frame, third ingredient must belong to ingredient type "Deglazing Liquids." The ingredients belonging to ingredients type "Deglazing Liquids" are additionally filtered and ranked according to their compatibility match with the selected matching ingredient, first ingredient AND second ingredient.

| Deglazing Liquids |
| --- |
| Cider |
| Apple Juice |
| Cola |
| Beer |
| Sherry |
| Orange juice |
| Pouilly-Fume |
| Pineapple juice |
| Fiano |
| Shiraz - Australia |
| Cherry juice |
| Sancerre |
| Champagne - France |
| Sauvignon Blanc |
| Chablis - France |
| Cucumber juice |
| Pinot noir |
| Cabernet Sauvignon - France |
| Tomato juice |
| Palm wine |
| Sauternes |
| Rice wine |
| Cabernet-Merlot - Italy |
| Gewurztraminer |
| Tempranillo |

Step 6: Fourth Ingredient Selection

According to composition frame, fourth ingredient must belong to ingredient type "Herbs." The ingredients belonging to ingredients type "Herbs" are additionally filtered and ranked according to their compatibility match with the selected matching ingredient, first, second AND third ingredient.

| Herbs |
| --- |
| Bay leaf - fresh - India |
| Tagetes - fresh |
| Orris root - dried |
| Tarragon - fresh |
| Sesame seed - roasted |
| Paracress - fresh |
| Rice paddy herb |
| Lovage - fresh |
| Oregano - dried |
| Shiso - fresh - Japan |
| Epazote - fresh - Mexico |
| Caraway seed - dried |
| Anise hyssop - fresh |
| Grains of paradise - dried |
| Majoram sweet - fresh |
| Nutmeg |
| Boldo - dried - Chile |
| Parsley leaves - fresh |
| Lovage root - dried |
| Caraway - dried |
| Kaffir lime leaf - dried |
| Grains of Selim - dried |
| Bay leaf - fresh |
| Cardamom - dried |
| Pepper |

| Selection | | Taste1 | Taste2 | Taste3 | Taste4 |
| --- | --- | --- | --- | --- | --- |
| Ingredient 1 | Shellfish fumet | 81.5 | 5.2 | 0.85 | 43.4 |
| Ingredient 2 | Parsnip - fresh | 0 | 83 | 16.5 | 0 |
| Ingredient 3 | Pouilly Fume | 0 | 0.4 | 88.4 | 10.7 |
| Ingredient 4 | Tarragon - fresh | 0 | 0 | 0 | 100 |

Calculation

Quantities of ingredients for approaching the characteristic are obtained by constructing an optimization problem.

| Selection | | Proportion |
| --- | --- | --- |
| Ingredient 1 | Shellfish fumet | 0.553 |
| Ingredient 2 | Parsnip - fresh | 0.253 |
| Ingredient 3 | Pouilly Fume | 0.113 |
| Ingredient 4 | Tarragon - fresh | 0.081 |

| | Taste1 | Taste2 | Taste3 | Taste4 |
| --- | --- | --- | --- | --- |
| obtained characteristic of end product | 45.07 | 23.92 | 14.63 | 33.31 |

|  | Taste1 | Taste2 | Taste3 | Taste4 |
|---|---|---|---|---|
| Desired characteristic of end product | 44.78 | 24.01 | 15.13 | 33.56 |

Euclidian distance: 0.58

Rescaling to a Desired End Mass

| Selection | Quantities | |
|---|---|---|
| Ingredient 1 | Shellfish fumet | 1000 ml |
| Ingredient 2 | Parsnip - fresh | 450 g |
| Ingredient 3 | Pouilly Fume | 205 ml |
| Ingredient 4 | Tarragon - fresh | 15 g |

Example 6

Step 1: Ingredient Selections

User selects a set of ingredients to be included in a recipe (or e.g. has this ingredients available in his kitchen)

| Selection | Ingredients |
|---|---|
| Ingredient 1 | Dark chocolate 70% |
| Ingredient 2 | Gin |
| Ingredient 3 | Tomato juice |
| Ingredient 4 | Lemon juice |
| Ingredient 5 | Thyme |

Based on the ingredient type of the selected ingredients and their characteristics, a list of physically possible End product types/End characteristics can be filtered and ranked and provided to the user for further selection thereof.

Step 2: End Characteristic Selection

| End characteristic |
|---|
| Cocktail - Long drink style |
| Chocolate confections - Moldable type - fruit based |
| Chocolate confections - Moldable type - Alcohol based |
| Cocktail - Martini style |
| Sauce - Veggie based |
| Cocktail - Sweet & Sour style |

According to the selected End product type and/or End characteristic, some of the selected ingredient may not be possible to include in the final recipe. Additionally it may be possible that extra ingredients are required in order to reach the desired end characteristic sufficiently. The selection of extra ingredients may be a user input, or can be automated.

According to user selection: the following results can be obtained:

Long Drink:
50 ml Gin
15 ml syrup*
25 ml lemon juice
80 ml tomato juice
chocolate garnish
Fill a Long drink glass with ice cubes.
Built the cocktail in a glass. Stir slightly. Finish with a some sprinkles of chocolate
* syrup was added automatically in order to reach the desired end characteristic Chocolate Confections—Moldable Type—Fruit Based
1000 g Dark chocolate 70%
600 g butter*
270 g tomato juice
540 g invert sugar*
25 g thyme
Bring tomato juice, invert sugar and thyme to a boil. Strain. Pour on the dark chocolate, temperature should not go over 50° C. Stir in the butter at 38° C. Allow to cool.
* ingredients added to reach the desired end characteristic Chocolate Confections—Moldable Type—Alcohol Based
1000 g Dark chocolate 70%
600 g butter*
90 g gin
90 water*
30 lemon juice
580 g invert sugar*
25 g thyme
Bring water, invert sugar and thyme to a boil. Add the gin and lemon juice. Strain. Pour on the dark chocolate, temperature should not go over 50° C. Stir in the butter at 38° C. Allow to cool.

Cocktail—Martini Style
50 ml Gin
2 g sugar*
20 ml tomato juice
lemon garnish
Put all ingredients in a stir glass with ice. Stir for 30 seconds. Strain in a glass. Finish with a wedge of lemon.
* sugar was added automatically in order to reach the desired end characteristic Sauce—Veggie Based
600 g onion
25 g thyme
300 g gin
4.5 l tomato juice
2.25 l beef stock
100 g chocolate
Braise the onion and thyme, deglaze with 300 g of gin and 4.5 l tomato juice. Deglaze to one third of the volume. Add the beef stock and reduce to desired thickness.
Take 1 L of sauce base and finish with chocolate Cocktail—Sweet & Sour style
60 ml Gin
20 ml syrup
20 ml lemon juice
Thyme garnish
Put all ingredients in a shaker with ice. Shake for 30 seconds. Strain in a glass. Finish with a sprig of thyme.
* syrup was added automatically in order to reach the desired end characteristic

We claim:

1. A method comprising:
    by a computer, with a processor and memory,
    receiving, from a user via an interface an end product, wherein each end product comprises a plurality of ingredients, wherein each ingredient is associated with at least a characteristic selected from the group consisting of a taste, a flavor, a smell, a texture, or a color, and a combination thereof;
    receiving, from the user and via the interface, a desired characteristic of the end product, wherein the desired characteristic is entered by the user or selected by the user from one or more desired characteristics, and wherein the one or more desired characteristics are selected from the group consisting of a taste, a flavor, a smell, a texture, or a color, and a combination thereof;

receiving, from the user and via the interface, a first ingredient, wherein the first ingredient is selected by the user from one or more ingredient options from a composition frame related to the desired characteristic of the end product;

updating the composition frame, based on the first ingredient, wherein the updating of the composition frame includes correlation of ingredients ranked by gas chromatography and mass spectrometer rankings; and receiving, from the user via the interface, at least one second ingredient, wherein the at least one second ingredient is selected by the user from one or more second ingredients from the updated composition frame related to the desired characteristic of the end product.

2. The method of claim 1, further comprising:
receiving, from the user and via the interface, a selection for the preparation method to be applied to the first ingredient or the at least second ingredient before they are combined to create an actual characteristic that approaches the desired characteristic.

3. The method of claim 2, wherein the preparation method is selected from the group consisting of a cooking technique, a cocktail preparation technique, a baking technique, a processing technique, and a combination thereof.

4. The method of claim 2, further comprising:
providing, to the user via the interface, a plurality of preparation methods based on the first ingredient or the at least second ingredient, whereby the first ingredient or the at least second ingredient is prepared according to the preparation method before they are combined to create an actual characteristic that approaches the desired characteristic.

5. The method of claim 1, further comprising:
rendering a food or drink recipe comprising the first ingredient at a first quantity and the at least one second ingredient at a second quantity, wherein the first and second quantities are suitable for creating an actual characteristic that approaches the desired characteristic.

6. The method of claim 5, wherein the quantity of one of the ingredients is determined additionally based on a desired intensity value of the ingredient in the end product.

7. The method of claim 6, wherein the quantity of each ingredient is determined such that an absolute intensity of each of the ingredients is identical.

8. The method of claim 1, further comprising:
receiving, from the user and via the interface, at least one third ingredient, wherein the at least one third ingredient is entered by the user or selected by the user from one or more third ingredients and is suitable, when combined with the first ingredient and the at least second ingredient, for creating an actual characteristic that approaches the desired characteristic.

9. The method of claim 8, further comprising:
rendering a food or drink recipe comprising the first ingredient at a first quantity, the at least one second ingredient at a second quantity, and the at least one third ingredient at a third quantity, wherein the first, second and third quantities are suitable for creating an actual characteristic that approaches the desired characteristic.

10. The method of claim 1, wherein the computer device is selected from the group consisting of a networked device, a local device, a vending machine, a food dispensing machine, a drink dispensing machine, an automated drink maker, an automated cocktail maker, an automated food preparation machine, a desktop computer, a laptop computer, a mobile device, a handheld device, a tablet, an iPad, a Kindle, a cellular phone, a smart phone, a personal digital assistant (PDA), a networked television, a networked media player, and a networked digital video recorder (DVR).

11. The method of claim 1, wherein the one or more second ingredients are compatible with the first ingredient selected by the user.

12. The method of claim 1, wherein each of the one or more second ingredients has a compatibility score with the first ingredient that is above a set value.

13. A method, comprising:
by a computer, with a processor and memory,
receiving, from a user via an interface on the computer, one or more ingredients from a composition frame stored in a relationship matrix related to, an end product characteristic, wherein the end product characteristic is selected from a list;
updating the composition frame, based on the one or more received ingredients,
wherein the updating of the composition frame includes correlation of ingredients ranked by gas chromatography and mass spectrometer rankings;
receiving a further ingredient from the updated composition frame; and
providing to the user via the interface, a food or drink recipe based on the one or more ingredients, the end product characteristic, and the further ingredient from the updated composition frame, comprising a quantity for each of the one or more ingredients in the recipe end characteristic.

14. The method of claim 13, further comprising:
providing, to the user via the interface, the preparation method based on the composition frame, one or more ingredient or the at least further ingredient, whereby the one or more ingredient or the at least further ingredient is prepared according to the preparation method before they are combined to create an actual characteristic that approaches the desired characteristic.

15. A method comprising:
by a computer, with a processor and memory, in communication with a data storage,
allowing selection, via an interface on a computer device, a type of end product, wherein the end product is selected by a user from one or more end products;
allowing selection, via the interface, of a desired characteristic of the end product, wherein the one or more desired characteristics are selected from the group consisting of a taste, a flavor, a smell, a texture, or a color, and a combination thereof, and wherein each desired characteristic is represented by a numerical value;
allowing selection, via the interface, of a first ingredient the end product, wherein the first ingredient is selected by the user from one or more first ingredients correlated in the data storage to the first ingredient in the end product based on gas chromatography and mass spectrometer rankings;
allowing selection, via the interface, at least one second ingredient based on gas chromatography and mass spectrometer correlation to the first ingredient and desired characteristic of the end product.

16. The method of claim 15, further comprising:
causing, via the interface, a food or drink recipe to be rendered, wherein the food or drink recipe comprises the first ingredient at a first quantity and the at least one second ingredient at a second quantity.

17. The method of claim 15, further comprising:
receiving, via the interface, the preparation method based on the first ingredient or the at least second ingredient, whereby the first ingredient or the at least second ingredient is prepared according to the preparation method before they are combined to create an actual characteristic that approaches the desired characteristic.

18. The method of claim 15, further comprising:
selecting, via the interface, a composition frame, wherein the composition frame comprises one or more ingredient types for further selection.

19. A system, comprising:
one or more processors; and
a non-transitory computer readable storage medium storing instructions which, when executed by the one or more processors, cause the one or more processors to perform operations comprising:
causing storage in a database information of different types of end products,
receiving a selection of a type of end product;
receiving a selection of a desired characteristic of the end product, wherein the desired characteristic is selected from the group consisting of a taste, a flavor, a smell, a texture, or a color, and a combination thereof, and wherein the desired characteristic is represented by a numerical value;
providing one or more first ingredients correlated to the selected type of end product based on gas chromatography and mass spectrometer data regarding the desired characteristic of the end product;
receiving a selection of one or more of the first ingredients;
providing one or more second ingredients based on gas chromatography and mass spectrometer data correlated between the first ingredient and desired characteristic of the end product; and
calculating quantities of the selected first and second ingredients, based on the desired characteristic of the end product characteristic,
wherein at least one of the selected first and second ingredient is subject to a method of preparation selected from the group consisting of a cooking technique, a cocktail preparation technique, a baking technique, a processing technique, and a combination thereof.

20. The system of claim 19, wherein the operations further comprising:
receiving a selection of the preparation method for at least one of the one or more first ingredients or the one or more second ingredients.

21. The system of claim 19, wherein the providing the one or more second ingredients is adapted for linking the type of end product to a composition frame consisting of a number of ingredient types and for repeating providing a selection and allowing selecting of one or more second ingredients until at least one ingredient is selected for each ingredient type by its compatibility with the first ingredient and/or one or more or all of the already selected second ingredients.

* * * * *